(12) United States Patent
Lindberg et al.

(10) Patent No.: US 8,224,058 B2
(45) Date of Patent: Jul. 17, 2012

(54) MEASUREMENT APPARATUS, METHOD AND COMPUTER PROGRAM

(75) Inventors: Stellan Lindberg, Förslov (SE); Tom Olesen, Görlöse (DK)

(73) Assignee: HemoCue AB, Angelholm (SE)

( * ) Notice: Subject to any disclaimer, the term of this patent is extended or adjusted under 35 U.S.C. 154(b) by 986 days.

(21) Appl. No.: 11/822,159

(22) Filed: Jul. 2, 2007

(65) Prior Publication Data

US 2008/0019584 A1 Jan. 24, 2008

Related U.S. Application Data

(60) Provisional application No. 60/907,897, filed on Apr. 20, 2007.

(30) Foreign Application Priority Data

Jul. 19, 2006 (SE) ........................................ 0601575
Apr. 20, 2007 (SE) ........................................ 0700958

(51) Int. Cl.
*G06K 9/00* (2006.01)

(52) U.S. Cl. .......................... 382/133; 382/100; 382/134

(58) Field of Classification Search ................... 382/100, 382/128, 190, 224
See application file for complete search history.

(56) References Cited

U.S. PATENT DOCUMENTS

| | | | |
|---|---|---|---|
| 4,338,024 A | 7/1982 | Bolz et al. | |
| 4,477,346 A * | 10/1984 | Dickinson et al. | 210/198.2 |
| 4,528,274 A | 7/1985 | Carter et al. | |
| 4,786,165 A * | 11/1988 | Yamamoto et al. | 356/23 |
| 5,123,055 A | 6/1992 | Kasdan | |
| 5,170,182 A * | 12/1992 | Olson et al. | 347/231 |
| 5,262,302 A | 11/1993 | Russell | |
| 5,436,978 A * | 7/1995 | Kasdan | 382/133 |
| 5,585,246 A | 12/1996 | Dubrow et al. | |
| 5,671,290 A * | 9/1997 | Vaidyanathan | 382/133 |
| 6,804,385 B2 | 10/2004 | Eisfeld et al. | |
| 6,943,839 B1 * | 9/2005 | Matsumoto et al. | 348/333.01 |
| 7,782,447 B2 * | 8/2010 | Lindberg | 356/39 |

(Continued)

FOREIGN PATENT DOCUMENTS

CA 2 514 055 2/2004

(Continued)

OTHER PUBLICATIONS

International-Type Search Report dated Jul. 19, 2006 for International Application No. 0601575-4.

(Continued)

*Primary Examiner* — Chan S Park
*Assistant Examiner* — Avinash J Yentrapati
(74) *Attorney, Agent, or Firm* — Buchanan Ingersoll & Rooney

(57) ABSTRACT

A measurement apparatus for enumeration of particles or white blood cells in a sample comprises: a holder, which is arranged to receive a sample acquiring device that holds a sample, an imaging system, comprising a magnifying means and at least one digital image acquiring means, said imaging system being arranged to acquire at least one digital image of the sample, and an image analyser, which is arranged to analyse the digital image for identifying particles or white blood cells and determining the number of particles or white blood cells and which is arranged to analyse the digital image for identifying particles or white blood cells that are imaged in focus, determining types of these particles or white blood cells, the types being distinguished by physical features and determining the ratio of different types of particles or white blood cells.

24 Claims, 7 Drawing Sheets

U.S. PATENT DOCUMENTS

| | | | |
|---|---|---|---|
| 2002/0177885 A1* | 11/2002 | Eisfeld et al. | 607/89 |
| 2003/0197112 A1* | 10/2003 | Atkinson et al. | 250/201.6 |
| 2004/0126008 A1* | 7/2004 | Chapoulaud et al. | 382/156 |
| 2004/0241677 A1* | 12/2004 | Lin et al. | 435/6 |
| 2005/0048657 A1* | 3/2005 | Young et al. | 436/16 |
| 2005/0183496 A1* | 8/2005 | Baek | 73/54.09 |
| 2005/0185832 A1* | 8/2005 | Douglass et al. | 382/133 |
| 2005/0197405 A1* | 9/2005 | Li et al. | 514/680 |
| 2005/0234656 A1* | 10/2005 | Schwartz et al. | 702/20 |
| 2005/0286026 A1* | 12/2005 | Matsumoto et al. | 353/101 |
| 2006/0210428 A1* | 9/2006 | Lindberg et al. | 422/58 |
| 2006/0257883 A1* | 11/2006 | Bjoraker et al. | 435/6 |
| 2008/0019584 A1* | 1/2008 | Lindberg et al. | 382/134 |
| 2008/0160566 A1* | 7/2008 | Lindberg et al. | 435/40.51 |
| 2009/0011518 A1* | 1/2009 | Lindberg | 436/172 |

FOREIGN PATENT DOCUMENTS

| | | |
|---|---|---|
| CA | 2 714 903 | 7/2009 |
| JP | 7020124 A | 1/1995 |
| JP | 9089752 A | 4/1997 |
| JP | 10185803 A | 7/1998 |
| JP | 11295208 A | 10/1999 |
| JP | 2002-148261 A | 5/2002 |
| JP | 2004347861 A * | 12/2004 |
| RU | 2200945 C2 | 3/2003 |
| RU | 2246728 C2 | 10/2004 |
| WO | 97/02482 | 10/1997 |
| WO | 98/50777 | 11/1998 |
| WO | WO-99/08091 A1 | 2/1999 |
| WO | WO-99/24831 A1 | 5/1999 |
| WO | 99/45384 | 9/1999 |
| WO | WO-99/45384 A1 | 9/1999 |

OTHER PUBLICATIONS

English translation of Official Action issued in Japanese Patent Application No. 2009-520705 mailed Feb. 15, 2011.

Australian Examiner's Report issued in Australian Patent Application No. 2007275927 mailed Mar. 16, 2011.

Notice to File a Response issued in corresponding Korean Patent Application No. 10/2009-7002990 dated Feb. 14, 2011 and English translation.

Decision on Grant (Notice of Allowance) in corresponding Russian Application No. 2009105673/14(007582), issued Apr. 23, 2010.

Office Action issued May 5, 2011 in corresponding Canadian Application No. 2,655,024.

English language translation of Japanese Office Action issued Jan. 20, 2012 in JP Appln No. 2009-520705.

* cited by examiner

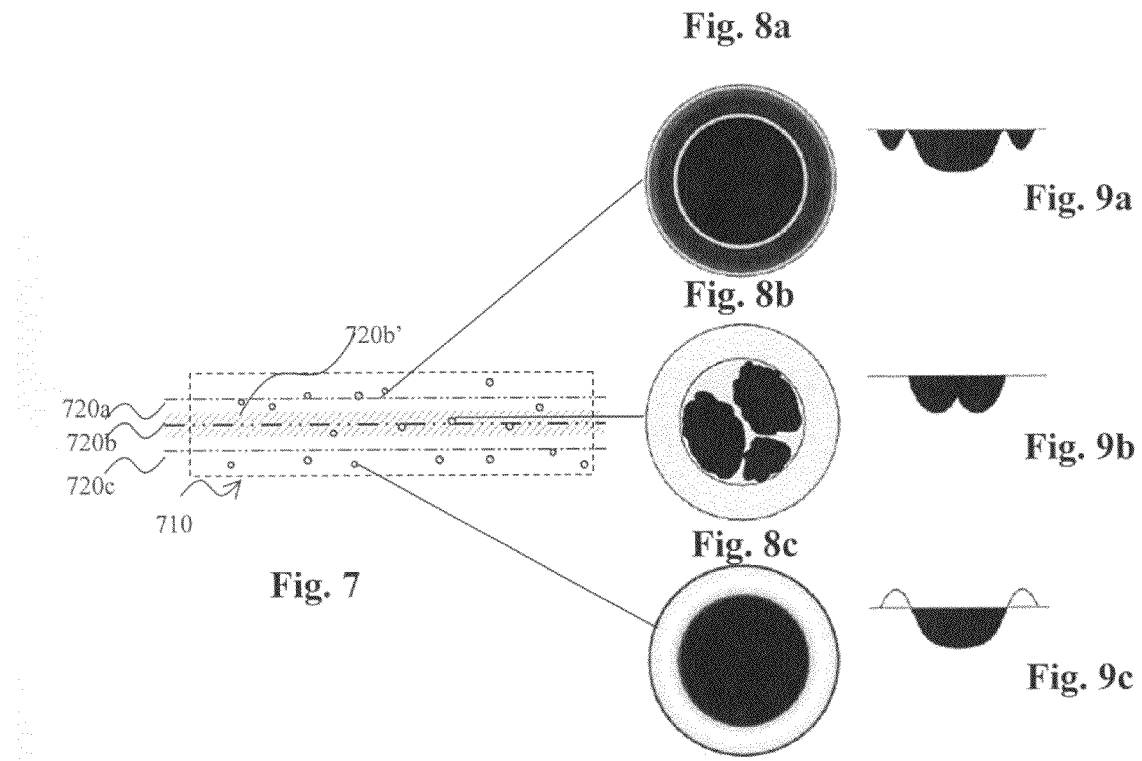

MEASUREMENT APPARATUS, METHOD AND COMPUTER PROGRAM

The benefit is claimed under 35 U.S.C. §119(a)-(d) of Swedish Application No. 0601575-4, filed Jul. 19, 2006 and Swedish Application No. 0700958-2, filed Apr. 20, 2007, and under 35 U.S.C. §119(e) of U.S. Provisional Application No. 60/907,897, filed Apr. 20, 2007.

TECHNICAL FIELD

The present invention relates to a measurement apparatus and a method for enumeration of particles, such as white blood cells in a sample, such as a blood sample. The present invention further relates to a computer program for analysing a sample.

BACKGROUND OF THE INVENTION

Determining a white blood cell count is often important in connection to treating a patient. This analysis may be needed for diagnosing e.g. leukaemia, or infectious or inflammatory diseases or for monitoring treatments. It is desirable to enable analysis results to be obtained as quickly as possible in order to minimize waiting times for patients and enabling a physician to make a decision of treatment and diagnosis directly when making a first examination of the patient. It would therefore be preferable to provide an analysis method which may be quickly performed by the physician or a nurse without the need of sending a test away to a laboratory. Determining the white blood cell count is one of the most common tests being performed on patients in establishing a diagnosis. Therefore, it would be very advantageous to have a quick and simple method of performing the analysis.

Today, a white blood cell count is normally obtained through a manual procedure by staining a blood sample and microscopically viewing the sample in a special counting chamber, e.g. a Bürker chamber. The counting chamber is provided with a grid dividing the chamber in well-defined small volumes. The white blood cells are allowed to settle at the bottom of the counting chamber in order to enable the microscope to focus on all cells in the chamber and, thus, facilitate counting. Thus, the sample needs to settle for several minutes before the counting may be performed. The white blood cell count can then be determined by counting the number of blood cells per box in the grid. The white blood cell count is obtained manually by an analyst, who needs to be experienced in performing the analysis in order to be able to perform a reliable analysis.

This analysis is time-consuming. Further, since it is performed manually, the results of the analysis may vary depending on the person performing the analysis.

There are a few number of existing automated analysis methods for determining a white blood cell count. The white blood cell count may be determined by means of the Coulter principle, which is based on determining cell size and thereby the cell type by sensing an impedance. A method for counting white blood cells by the Coulter principle is described in U.S. Pat. No. 5,262,302. Measurement apparatus according to the Coulter principle is expensive and it is therefore a considerable investment. Thus, a hospital or laboratory will be reluctant to invest in more than one apparatus. This implies that the analysis will need to be performed in a centralised location and a patient will need to wait for analysis results.

The Coulter principle is the dominating, automated analysis method that is presently being used. However, there are a few other methods that have been described. One such method for determining a white blood cell count is disclosed in U.S. Pat. No. 5,585,246. Here, a blood sample has to be prepared by being mixed with a fluorescent dye and ligand complex which tags the white blood cells. The sample is introduced into a capillary and is irradiated by a laser source which scans over the sample in the capillary. The fluorescence is measured in order to determine the number of white blood cells. A similar method is disclosed in WO 97/02482, using a fluorescent dye and a laser source scanning over a capillary. This method is adapted for enumeration of white blood cells in apheresis products containing a low number of white blood cells. Here, the capillary is quite thick and it is necessary to wait until the white blood cells have settled at the bottom of the capillary before the capillary may be scanned.

In WO 99/45384, a sample-containing chamber having varying thickness is shown. The varying thickness separates different compounds of blood. The blood sample is stained with a colorant to differentially highlight at least three different white blood cell types in the blood sample. The white blood cells may be enumerated by using an optical scanning instrument to view a portion of the chamber.

In WO 98/50777, a method for assessment of the number of somatic cells in milk is disclosed. The method comprises applying a volume of a sample in a sample compartment and transmitting electromagnetic signals, having passed from the sample compartment, onto an array of detection elements. The intensities of detected electromagnetic signals are processed and the results are correlated to the number of cells present in the sample.

There is still a need to speed up and simplify existing automated methods for determining a white blood cell count such that the analysis may be performed by any user, not requiring special training, and such that measurement apparatuses may be relatively inexpensive. This would imply that the analysis may be provided at a point of care. Further, since the white blood cell count is such a commonly performed analysis, any improvement to the analysis method would have a positive impact on patient care. An analysis method providing a possibility to obtain results at a point of care would be particularly advantageous.

Also, it may be advantageous to obtain a differential white blood cell count, that is to examine the distribution of different types of white blood cells in a blood sample. This differential white blood cell count may reveal if the cells are present in a normal distribution, or if any cell type is increased or decreased. The information may be useful in diagnosing specific types of illness. For example, an increase in neutrophils indicates a bacterial infection, whereas an increase in lymphocytes is common in acute viral infections.

The differential white blood cell count may also be obtained by microscopically viewing and manually counting stained blood cells in a Bürker chamber. There also exist some automated methods. For example, a differential count may be obtained with the Coulter principle by analysing the form and size of the electrical pulse generated by a cell passing through an electrical field. The form and size of the pulse may be related to the type of white blood cell being detected. One such method is described in U.S. Pat. No. 4,528,274.

In U.S. Pat. No. 5,123,055, another method for identifying different types of white blood cells is described. This method requires several size and colour parameters to be sequentially analysed in order to differentiate the types of white blood cells.

It is still desired to speed up and simplify existing automated methods for determining a differential white blood cell count. It would be particularly advantageous to provide a quick, simple and relatively inexpensive analysis method such that the analysis may be provided at a point of care.

SUMMARY OF THE INVENTION

It is an object of the invention to provide a simple analysis for determining a volumetric enumeration of particles, such as white blood cells in a sample, such as a blood sample and determining a differential particle count, such as a differential white blood cell count.

Thus, according to one aspect of the invention, there is provided a measurement apparatus for enumeration of particles, such as white blood cells in a sample, such as a blood sample.

The apparatus comprises a holder, which is arranged to receive a sample acquiring device comprising a measurement cavity that holds a sample, an imaging system adapted to acquire at least one magnified digital image of the sample. The apparatus further comprises an image analyser, which is arranged to analyse the at least one acquired digital image for identifying the particles and determining the number of particles in the sample, wherein the image analyser is arranged to analyse the at least one acquired digital image for identifying particles that are imaged in focus and determining types and number of these particles, the types being distinguished by physical features of the particles, whereby the ratio of different types of particles in the sample is determined.

The imaging system may comprise a magnifying means and at least one digital image acquiring means.

In accordance with one embodiment the apparatus is adapted for enumeration of white blood cells in a blood sample, the measurement cavity is adapted to hold a stained and hemolysed blood sample, and wherein the image analyser is arranged to analyse the at least one acquired digital image for identifying stained white blood cells and determining the number of white blood cells in the sample, wherein the image analyser is arranged to analyse the at least one acquired digital image for identifying white blood cells that are imaged in focus and determining types and number of these white blood cells, the types being distinguished by geometric features of the white blood cells, whereby the ratio of different types of white blood cells in the sample is determined.

According to another aspect of the invention, there is provided a method for enumeration of particles in a sample, said method comprising: acquiring a sample into a measurement cavity of a sample acquiring device, acquiring at least one digital image of a magnification of the irradiated sample in the measurement cavity, digitally analysing the at least one digital image for identifying the particles and determining the number of particles in the sample, and digitally analysing the at least one digital image for identifying particles that are imaged in focus and determining types and number of these particles, the types being distinguished by geometric features of the particles, whereby the ratio of different types of particles in the sample is determined.

In accordance with one embodiment the method is adapted for enumeration of white blood cells in a blood sample. The method comprises acquiring a blood sample into a measurement cavity of a sample acquiring device. The blood sample is mixed with a reagent, comprising a hemolysing agent for lysing the red blood cells in the blood sample and a staining agent for staining the white blood cells in the blood sample. The staining agent preferably selectively stains white blood cells and does not stain other cells in the blood sample. The method further comprises acquiring at least one digital image of a magnification of the sample in the measurement cavity. The method further comprises digitally analysing the at least one digital image for identifying stained white blood cells and determining the number of white blood cells in the sample, and digitally analysing the at least one digital image for identifying white blood cells that are imaged in focus and determining types and number of these white blood cells, the types being distinguished by geometric features of the stained cells, whereby the ratio of different types of white blood cells in the blood sample is determined.

The measurement apparatus and the method of the invention both enable simple analysis of a sample of whole blood. To this end, the measurement apparatus is arranged to acquire at least one digital image of a blood sample, which sample has been mixed with a staining agent for staining the white blood cells. The staining of the white blood cells implies that the white blood cells may be distinguished in a digital image and different types of white blood cells may be distinguished by geometric features of the cells in the same or another digital image.

The measurement apparatus and the method are thus arranged to both determine a volumetric enumeration of all white blood cells within the blood sample and determine a differential white blood cell count.

Whereas many existing methods are able to count different blood cells and even subgroups of blood cells, the measurement apparatus according to the invention is specifically adapted to analysis of white blood cells. The reagent comprises a hemolysing agent which will lyse the red blood cells in the blood sample. This destroys the possibilities to enumerate the red blood cells in the sample. On the other hand, the lysing of the red blood cells simplifies the distinguishing and identification of the white blood cells within the blood sample.

Further, the measurement apparatus is specifically adapted to analyse the at least one digital image such that cells that are imaged in focus are identified. This allows an image to be acquired of a relatively thick sample, while only the cells that are in focus are counted. This feature is particularly useful considering that the enumeration of the total number of white blood cells is more easily made than the identification of the type of white blood cells, since typing requires more details of the cell to be analysed. Thus, by ensuring that only cells that are in focus are counted, the identification of the type of white blood cells may be performed in a sample that may simultaneously be used for determining a statistically reliable volumetric enumeration of the white blood cells in the sample.

The measurement apparatus and the method of the invention provide a very simple analysis of a sample of whole blood. The analysis does not require complicated measurement apparatus or advanced steps to be performed by an operator. Therefore, it may be performed in direct connection to examination of a patient, without the need for a qualified technician. It is merely required that a blood sample is acquired and mixed with a staining agent. Then, the blood sample may be placed in the holder of the measurement apparatus and, in direct response thereto, the measurement apparatus may present analysis results.

In fact, the blood sample may be allowed to be mixed with the reagent in the measurement cavity. Thus, there will be no need to perform a sample preparation manually. Within a few minutes or less, the reaction of the blood sample with the reagent will have hemolysed the red blood cells and stained the white blood cells such that the sample is ready for optical measurement to acquire the at least one digital image. The blood sample may be mixed with the reagent by e.g. dispersion or diffusion of the reagent into the blood sample or by actively vibrating or moving the sample acquiring device so that an agitation is caused in the measurement cavity.

The measurement apparatus may further comprise an electromagnetic radiation source, which is arranged to irradiate the sample held in the measurement cavity of the sample acquiring device.

The imaging system may be arranged to acquire a plurality of digital images of the sample using different optical settings, wherein the image analyser is arranged to analyse each acquired digital image for identifying particles or stained white blood cells and determining the number of particles or white blood cells in the sample, wherein the image analyser is arranged to analyse each acquired digital image for identifying particles or white blood cells that are imaged in focus and determining types and number of these particles or white blood cells, the types being distinguished by geometric features of the particles or stained white blood cells, whereby the ratio of different types of particles or white blood cells in the sample is determined.

By acquiring a plurality of digital images at different levels in the direction of depth of field in the sample, it is possible to analyse a relatively large sample volume even when using a high magnification. A high magnification makes it, due to the resulting small depth of field, difficult to view the complete volume in one image. Since the magnification level affects the depth of field, the step of acquiring a plurality of digital images allows the use of a greater magnification, which in turn makes it possible to, in each image, differentiate between different kinds of white blood cells depending, amongst others, upon the shape, number or size of the nuclei.

According to another embodiment, the imaging system is arranged to provide information about the direction of light in the acquired image to facilitate focusing, whereby shifting focus in the acquired image is enabled. This implies that a single image may be used both for enumeration of the total number of white blood cells in the sample analysing the entire depth of the sample at once, and for determining the ratio of different types of white blood cells in the blood sample by analysing cells in the image when the image is shown with a portion of the thickness of the blood sample being in focus. An image comprising information of direction of light into the image may be obtained using an array of small lenses (e.g., a compound lens) providing ability to trace rays in the acquired image such that different parts of the image may be placed in focus.

The imaging system may be arranged to acquire a first and a second digital image of the sample using different optical settings, and wherein the image analyser is arranged to analyse the first acquired digital image for determining the number of particles or white blood cells in the sample and the image analyser is arranged to analyse the second acquired digital image for determining the ratio of different types of particles or white blood cells in the sample.

Thus, the measurement apparatus is specifically adapted to acquire two digital images using different optical settings. This implies that the optical settings may be optimised and adapted to, firstly, determine the number of white blood cells within a volume and, secondly, determine a ratio of different types of white blood cells.

The imaging system may comprise two at least partly separate parts, which direct light from an irradiated sample to a first and a second part of the imaging system.

The action to determine if a white blood cell is in focus or not may be performed by making use of the fact that the cytoplasm of the cell may act as a lens refracting the light. For a white blood cell imaged in focus the nuclei appear as dark shadows whereas the surrounding cytoplasm is almost invisible. The nuclei appear as regions with significantly lower light intensity whereas the cytoplasm leaves the light intensity unaffected.

For a white blood cell imaged too close to the imaging system (too close to be in focus) the nuclei appear as dark shadows whereas the surrounding cytoplasm acts as a lens and refracts the light which results in a dark circle around the nuclei. The nuclei appear as a region with significantly lower light intensity relative to a focused image of the nuclei and the cytoplasm appears with low light intensity.

For a white blood cell imaged too far away from the imaging system (too far to be in focus) the nuclei appear as dark shadows whereas the surrounding cytoplasm acts as a lens and refracts the light resulting in a bright circle around the nuclei. The nuclei appear as a region with significantly lower light intensity relative to a focused image of the nuclei whereas the cytoplasm appears with high light intensity.

Alternatively, the identifying of the cells that are imaged in focus may be performed by analysing the edges of imaged cells in order to assess whether the cell is imaged in focus based on a slope of intensity at the edge. Cells that are not in focus will show a slow decrease in intensity at the edges, whereas cells in focus will be imaged with a sharp edge represented as a large decrease in intensity at the edge of the cell. Thus, by analysing how the intensity varies at an edge of an imaged cell, it may be determined whether the cell is imaged in focus or not.

An alternative way to determine the cell type is by, in the image analyser, for a specific particle or cell, determining the number of said images in which said particle or cell is imaged counting from an image in which the particle or cell is determined to be out of focus in a first direction to an image in which the particle or cell is determined to be out of focus in a second direction.

The image analyser may be arranged to determine, based on the counted number of images, a geometrical feature related to the size of said particle or cell.

The imaging system with the optical settings used for acquiring said at least one digital image may have a magnification power of 1-50×, more preferably 1-20×, more preferably 3-20×, more preferably 5-20× and more preferably about 10×.

The imaging system may be arranged to obtain said at least one digital image with a depth of field in the range of 2-60 micrometers, more preferably in the range of 2-30 micrometers, more preferably about 8-10 micrometers.

As used in this context, "depth of field" implies a length in a direction along the optical axis that is imaged in a sufficient focus to allow image analysis to identify cells positioned within this length. This "depth of field" may be larger than a conventional depth of field defined by the optical settings. With an increased magnification power, the depth of field is decreased.

The electromagnetic radiation source may be arranged to irradiate a wavelength corresponding to a peak in absorbance of the staining agent. Consequently, the stained white blood cells which contain an accumulation of staining agent will be detected by an indication of a low transmittance of light in the digital images.

The electromagnetic radiation source may comprise a laser source. The laser source may provide light of a well-defined wavelength fitting the absorbance of the staining agent. Further, the laser source may provide collimated light, minimizing disturbances of stray light, such that a point of low transmittance of light will be sharply distinguished.

The electromagnetic radiation source may alternatively comprise a light emitting diode. This radiation source may still provide sufficient irradiating conditions for properly distinguishing white blood cells from other matter in the sample.

The image analyser may be arranged to identify areas of high light absorbance in order to determine the number of particles or white blood cells in the sample. The image analyser may be further arranged to identify black or dark dots in the image. Since the staining agents may be accumulated in the nuclei of the white blood cells, the absorbance of the light may have peaks at separate points. These points will form black dots in the digital image and may be classified as white blood cells.

The image analyser may be arranged to distinguish different types of particles or white blood cells by analysing shape and size of identified areas of high light absorbance in the at least one digital image. Since different types of white blood cells have different sizes, the type of a white blood cell may be identified by determining the size of the blood cell. Further, the different types may be differently stained giving different shapes of the identified areas in the digital image. This may also be used in order to identify the type of white blood cells. A differential white blood cell count specifying the ratio of three different types of white blood cells may be obtained by analysing the size of the blood cells. A differential white blood cell count distinguishing five different types of white blood cells may require further features of the blood cells to be investigated. For example, a number of nuclei of each cell, an intensity of radiation transmitted through the blood cell, or the shape of the blood cell may be examined.

The staining agent may be arranged to selectively stain the nuclei of the white blood cells. This implies that the white blood cells may be identified as coloured dots and therefore easily be distinguished and counted in a digital image. Further, the size of the stain spots may be used to identify the type of the white blood cells, as different types of white blood cells have different sizes.

The staining agent may be any one in the group of Hematoxylin, Methylene blue, Methylene green, Methylene azure, cresyl violet acetate, Toluidine blue, Gentian violet, Sudan analogues, Gallocyanine, and Fuchsin analogues, or any combination thereof. However, it should be appreciated that the staining agent is not limited to this group, but many other substances may be contemplated.

The hemolysing agent may be a quaternary ammonium salt, a saponin, a bile acid, such as deoxycholic acid, a digitoxin, a snake venom, a glucopyranoside or a non-ionic detergent of type Triton. However, it should be appreciated that the hemolysing agent is not limited to this group, but many other substances may be contemplated.

The measurement apparatus may further comprise an objective lens which is shared for the different optical settings. This implies that the digital images may be obtained by imaging along the same optical path such that the images are centered at the same point in the measurement cavity. This makes the measurement apparatus compact.

According to one embodiment, the imaging system may comprise two at least partly separate parts, which direct light from an irradiated sample to a first and a second part of the imaging system. This implies that the path of light from the sample to the imaging system may be defined within a fixed optical set-up. Thus, the measurement apparatus may be robust and insensitive to impact.

The imaging system may further comprise a beam splitter for directing light from the objective lens towards the first or the second part of the imaging system. This implies that the first and second digital images may be obtained simultaneously, whereby the analysis may be very quickly performed.

The first part of the imaging system may be arranged to receive light directly from the beam splitter, that is no optical element is arranged between the first part of the imaging system and the beam splitter. Alternatively, the light may be arranged to pass directly from the objective lens to the first part of the imaging system. Then, in order to obtain the second digital image, a mirror may be inserted into the light path for deflecting light to the second part of the imaging system instead.

The imaging system may further comprise an ocular lens between the beam splitter and the part of the imaging system adapted to acquire digital images. The ocular lens may thus provide a further magnification of the sample in order to distinguish between different types of white blood cells. Preferably, lens packages are used and the ocular lens package will then move a virtual principal plane within the objective lens package to change the relation between the image plane and the objective lens package to allow further magnification.

The imaging system may further comprise an optical element between the beam splitter and the part of the imaging system adapted to acquire digital images for affecting cells not positioned in focus of the imaging system, whereby identifying white blood cells that are imaged in focus is facilitated.

The optical element allows an image to be acquired of a sample thickness much larger than the depth of field of the imaging system. The optical element ensures that the cells that are out of focus may be withdrawn from consideration in order to increase the certainty of the measurement. Since the optical element affects the imaging of cells out of focus, the cells in focus will be easily identified. The optical element may be implemented as a spatial filter that affects the imaging of a cell such that the edge of the cell will comprise an overshoot intensity larger than the background intensity, where the cell is imaged by absorbing light.

According to an alternative embodiment, the imaging system may further comprise a wavefront coding element between the beam splitter and the second part of the imaging system. A wavefront coding element deliberately distorts the light rays by passing them through a waveplate with a saddle-like shape, that is relatively flat in the middle, but with scalloped edges. This causes a specific optical aberration, the image looks blurry, but the de-focus is the same over a large range of distances. This wavefront coding element thus increases a depth along the optical axis that may be analysed. The distortions in the image are mainly determined by the shape of the de-focusing wavefront coding element, which is accurately known. Therefore, a computer is able to remove the blur point by point. A computer may decode the image using what is essentially a digital filter, and thus creates an image which is sharp over a large depth of field. In this way, the depth of field of the imaging system may be increased, enabling a larger depth of a sample to be imaged in focus.

According to another embodiment, one part of the imaging system is arranged to acquire both the first and second images and at least part of the magnification system of the imaging system is switchable in order to acquire the first and second digital images using different optical settings. This implies that the measurement apparatus need only comprise one single part of the imaging system. Further, it allows several different optical settings to be used by e.g. providing a main lens that is movable between well-defined positions along the optical axis.

The imaging system may be arranged having a larger magnification power in the optical settings used for acquiring the second digital image than in the optical settings used for acquiring the first digital image. This implies that details may be better viewed in the second digital image, whereby different types of white blood cells may more easily be distinguished from each other.

The imaging system with the optical settings used for acquiring the first digital image may have a magnification power of 1-50×, more preferably 1-20×, more preferably 3-20×, more preferably 3-10× and more preferably about 4×. Within these ranges of magnification power, the white blood cells are sufficiently magnified in order to be detected, while the imaging system may be arranged to image the sample thickness within sufficient focus in order to assess the number of blood cells within the image. Thus, the imaging system may have a depth of field covering the sample thickness. However, the entire sample thickness need not be imaged within a depth of field of the imaging system, using a conventional definition of depth of field. Cells that are imaged slightly out of focus may still be correctly counted using clever image analysis. A low magnification power implies that a large "depth of field" may be obtained. Thus a large sample thickness may be allowed and a large volume may be analysed. However, if a low magnification power is used, the white blood cells may be hard to detect because each blood cell is imaged onto very few pixels, such as 3-4 pixels. A lower magnification power may be used by increasing the number of pixels in the acquired image, that is by improving the resolution of the digital image. In this way, it is possible to use an optical magnification power of 1-4×, while still enabling the white blood cells to be detected.

The imaging system with the optical settings used for acquiring the second digital image may have a magnification power of 1-50×, more preferably 1-20×, more preferably 3-20×, more preferably 5-20× and more preferably about 10×. Within these ranges of magnification power, the white blood cells are sufficiently magnified in order to distinguish between different types of white blood cells. A lower magnification power may be used by using an optical element for emphasizing cells that are imaged in focus and facilitating identification of these cells.

The imaging system may be arranged to obtain the first image with a depth of field of at least the thickness of the measurement cavity of the sample acquiring device. This implies that a sufficient focus is obtained of the entire sample thickness such that the entire thickness of the measurement cavity may be simultaneously analysed in the digital image of the sample. Thus, there is no need to await that the white blood cells settle in the measurement cavity, whereby the time for making an analysis is reduced. However, there may be a need to await a reaction causing the red blood cells to be hemolysed and await movements caused by introduction of the sample into the measurement cavity to settle. These waiting times would be very short, in the order of 30 seconds or less. By choosing not to focus very sharply on a specific part of the sample, a sufficient focus is obtained of the entire sample thickness to allow identifying the number of white blood cells in the sample. This implies that a white blood cell may be somewhat blurred and still be considered to be in focus of the depth of field. The analysed volume of the sample may thus be well-defined by the thickness of the measurement cavity and the size of the digital image specifying the cross-sectional area of the measurement cavity being imaged.

The imaging system may be arranged to obtain the first image with a depth of field in the range of 50-200 micrometers. This depth of field may be adapted to correspond to the depth or thickness of the measurement cavity. A depth of at least 50 micrometers allows a larger volume of blood to be analysed over a small cross-sectional area, thus avoiding compression of the blood cells of the sample into a monolayer. Thus, a sufficiently large volume of the blood sample in order to give reliable values of the white blood cell count may be analysed using a relatively small image of the blood sample. Further, it is difficult to achieve a depth of field exceeding 200 micrometers while obtaining a digital image with a sufficient magnification. It is even difficult to achieve a depth of field exceeding 170 micrometers.

The imaging system may be arranged to obtain the second image with a depth of field in the range of 2-60 micrometers. This may be achieved by imaging a portion of the thickness of the measurement cavity. In such case, only this portion of the thickness of the measurement cavity is imaged in focus. The second digital image is then analysed by only taking into account white blood cells that are imaged in sufficient focus in order to determine their type. Since the second digital image is used to determine the ratio of different types of white blood cells, it is not important to image a well-defined volume. Thus, it is possible to obtain appropriate first and second images by imaging the same portion of the measurement cavity. However, the second image may alternatively be acquired imaging a different portion of the measurement cavity, whereby this portion may have a thickness corresponding to the depth of field of the imaging system for obtaining the second image.

The image analyser may be arranged to electronically magnify the at least one acquired image. While the sample is being magnified for acquiring a magnified digital image of the sample, the acquired digital image itself may be electronically magnified for simplifying distinguishing between objects that are imaged very closely to each other in the acquired digital image.

According to another aspect of the invention, there is provided a sample acquiring device for enumeration of white blood cells in a blood sample. The sample acquiring device comprises a measurement cavity for receiving a blood sample. The measurement cavity has a first and a second predetermined fixed thickness defined between inner walls of the measurement cavity, wherein the first thickness is adapted for determining total volumetric enumeration of white blood cells in the blood sample and the second thickness is adapted for determining a ratio of different types of white blood cells within the blood sample. The sample acquiring device further comprises a reagent, which is arranged in a dried form on a surface defining the measurement cavity. The reagent comprises a hemolysing agent for lysing red blood cells in the blood sample, and a staining agent for selectively staining white blood cells in the blood sample.

The sample acquiring device provides a possibility to directly obtain a sample of whole blood into the measurement cavity and provide it for analysis. There is no need for sample preparation. In fact, the blood sample may be sucked into the measurement cavity directly from a pricked finger of a patient. Providing the sample acquiring device with a reagent enables a reaction within the sample acquiring device which makes the sample ready for analysis. The reaction is initiated when the blood sample comes into contact with the reagent. Thus, there is no need for manually preparing the sample, which makes the analysis especially suitable to be performed directly in an examination room while the patient is waiting.

Since the reagent is provided in a dried form, the sample acquiring device may be transported and stored for a long time without affecting the usability of the sample acquiring device. Thus, the sample acquiring device with the reagent may be manufactured and prepared long before making the analysis of a blood sample.

Whereas many existing methods are able to count different blood cells and even subgroups of blood cells, the sample acquiring device according to the invention is specifically adapted to performing enumeration of white blood cells. The reagent comprises a hemolysing agent which will lyse the red blood cells in the blood sample. This destroys the possibilities to enumerate the red blood cells in the sample. On the other hand, the lysing of the red blood cells simplifies the distinguishing and identification of the white blood cells within the blood sample.

The staining agent provides a marking of the individual white blood cells. This enables the white blood cells to be individually viewed or detected. The white blood cells may e.g. be detected by scanning the measurement cavity or obtaining an image of the measurement cavity.

The sample acquiring device further provides a first thickness of the measurement cavity specifically adapted to facilitate determining a volumetric white blood cell count. The measurement cavity may have a sufficient thickness to allow a quite large volume of the blood sample to be analysed and therefore allow a good statistic for determining the volumetric white blood cell count. The white blood cell count may thus be obtained by summing the number of individually detected white blood cells in a defined volume.

The sample acquiring device also provides a second thickness of the measurement cavity specifically adapted to facilitate distinguishing between different types of white blood cells. In this regard, the second thickness may be thinner than the first thickness allowing the entire second thickness to be imaged within a depth of field of a larger magnification. Such a larger magnification may be needed when distinguishing between different types of white blood cells in comparison to imaging in order to merely determine the total number of white blood cells, regardless of type, within the blood sample.

The sample acquiring device may comprise a body member having two planar surfaces forming inner walls to define said measurement cavity. The planar surfaces may be arranged at a predetermined distance from one another to determine a sample depth for an optical measurement. This implies that the sample acquiring device provides a well-defined depth to the optical measurement, which may be used for accurately determining the white blood cell count per volumetric unit of the blood sample. A volume of an analysed sample will be well-defined by the depth of the measurement cavity and an area of the sample being imaged. Thus, the well-defined volume could be used for associating the number of white blood cells to the volume of the blood sample such that the volumetric white blood cell count is determined.

The measurement cavity preferably has a first uniform depth of 50-200 micrometers. A depth of at least 50 micrometers implies that the measurement cavity does not force the blood sample to be smeared into a monolayer thereby allowing a larger volume of blood to be analysed over a small cross-sectional area. Thus, a sufficiently large volume of the blood sample in order to give reliable values of the white blood cell count may be analysed using a relatively small image of the blood sample. The first depth is more preferably at least 100 micrometers, which allows an even smaller cross-sectional area to be analysed or a larger sample volume to be analysed. Further, the first depth of at least 50 micrometers and more preferably 100 micrometers also simplifies manufacture of the measurement cavity having a well-defined depth between two planar surfaces.

For most samples arranged in a cavity having a thickness of no more than 200 micrometers, the white blood cell count is so low that there will be only minor deviations due to white blood cells being arranged overlapping each other. However, the effect of such deviations will be related to the white blood cell count and may thus, at least to some extent, be handled by means of statistically correcting results at least for large values of the white blood cell count. This statistical correction may be based on calibrations of the measurement apparatus. The deviations will be even less for a measurement cavity having a first thickness of no more than 170 micrometers, and even less for a measurement cavity having a first thickness of no more than 150 micrometers, whereby a simpler calibration may be used. This thickness may even not require any calibration for overlapping blood cells.

Further, the first thickness of the measurement cavity is sufficiently small to enable the measurement apparatus to obtain a digital image such that the entire depth of the measurement cavity may be analysed simultaneously. Since a magnifying system is to be used in the measurement apparatus, it is not easy to obtain a large depth of field. Therefore, the first thickness of the measurement cavity would preferably not exceed 150 micrometers in order for the entire thickness to be simultaneously analysed in a digital image. The depth of field may be arranged to handle a first thickness of the measurement cavity of 170 micrometers or even 200 micrometers.

The measurement cavity preferably has a second uniform thickness of 20-60 micrometers. This second thickness of the measurement cavity would allow the entire second thickness to be imaged within a depth of field of a magnification needed for distinguishing between different types of white blood cells. Further, the second thickness may still allow a sufficient volume to be imaged enabling a substantial number of white blood cells to be analysed. This would allow the ratio of different types of white blood cells to be determined with a good statistical certainty. Typically, it is desired to analyse the type of 200 white blood cells.

The sample acquiring device may be provided with a reagent that has been applied to the surface solved in a volatile liquid which has evaporated to leave the reagent in a dried form.

It has been realised that the reagent is advantageously solved in a volatile liquid before being inserted into the measurement cavity. This implies that the liquid may in an effective manner be evaporated from the narrow space of the measurement cavity during manufacture and preparation of the sample acquiring device. The reagent may preferably be arranged in a dried form in the part of the measurement cavity of the first thickness.

The reagent may preferably be solved in an organic solvent and more preferably be solved in methanol. Such solvents are volatile and may appropriately be used for drying the reagent onto a surface of the measurement cavity.

The sample acquiring device may further comprise a sample inlet communicating the measurement cavity with the exterior of the sample acquiring device, wherein the inlet is arranged to acquire a blood sample. The sample inlet may be arranged to draw up a blood sample by a capillary force and the measurement cavity may further draw blood from the inlet into the cavity. Also, the sample acquiring device may be arranged to first draw the sample into the portion of the measurement cavity of the first thickness. Part of the sample may then be further transported by capillary force into the portion of the measurement cavity of the second thickness. As a result, the blood sample may easily be acquired into the measurement cavity by simply moving the sample inlet into contact with blood. Then, the capillary forces of the sample inlet and the measurement cavity will draw up a well-defined amount of blood into the measurement cavity. Alternatively, the blood sample may be sucked or drawn into the measurement cavity by means of applying an external pumping force to the sample acquiring device. According to another alternative, the blood sample may be acquired into a pipette and then be introduced into the measurement cavity by means of the pipette.

The sample acquiring device may be disposable, i.e. it is arranged to be used once only. The sample acquiring device provides a kit for performing a white blood cell count, since the sample acquiring device is able to receive a blood sample and holds all reagents needed in order to present the sample to cell counting. This is particularly enabled since the sample acquiring device is adapted for use once only and may be formed without consideration of possibilities to clean the sample acquiring device and re-apply a reagent. Also, the sample acquiring device may be moulded in plastic material and thereby be manufactured at a low price rate. Thus, it may still be cost-effective to use a disposable sample acquiring device.

The invention also relates to a computer program product, embodied in a computer-readable medium, for analysis of a sample, comprising: computer code for digitally analyzing at least one image of a sample for determining a number of particles in the sample; computer code for digitally analyzing the at least one image of the sample for identifying one or more types of particles in a focused region of the sample, each type of particle being associated with one or more distinguishing physical features; and computer code for outputting information corresponding to the number and types of particles in the sample. The invention also relates to a computer program for analysing a sample, the computer program comprising computer program code for: analysing at least one digital image for identifying the particles and determining the number of particles in the sample, and analysing the at least one digital image for identifying particles that are imaged in focus and determining types and number of these particles, the types being distinguished by physical features of the particles, whereby the ratio of different types of particles in the sample is determined.

BRIEF DESCRIPTION OF THE DRAWINGS

The invention will now be described in further detail by way of example under reference to the accompanying drawings.

FIG. 7 illustrates a sample imaged at three different layers.

FIG. 8a illustrates a white blood cell in camera view when the cell is positioned out of focus of a measurement apparatus according to FIG. 10.

FIG. 8b illustrates a white blood cell in camera view when the cell is positioned in focus of a measurement apparatus according to FIG. 10.

FIG. 8c illustrates a white blood cell in camera view when the cell is positioned out of focus of a measurement apparatus according to FIG. 10.

FIG. 9a illustrates recorded intensities of a cross-section of a cell to be analysed, when the cell is positioned out of focus of a measurement apparatus according to FIG. 10.

FIG. 9b illustrates recorded intensities of a cross-section of a cell to be analysed, when the cell is positioned in focus of a measurement apparatus according to FIG. 10.

FIG. 9c illustrates recorded intensities of a cross-section of a cell to be analysed, when the cell is positioned out of focus of a measurement apparatus according to FIG. 10.

DETAILED DESCRIPTION OF PREFERRED EMBODIMENTS

Figure 1:
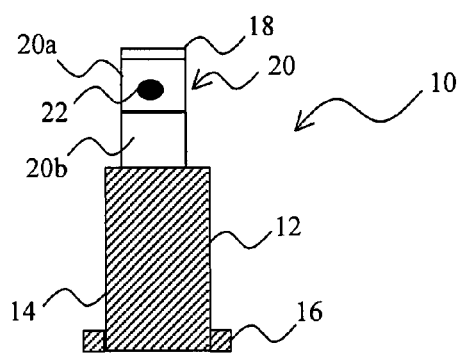
FIG. 1 is a schematic view of a sample acquiring device.

Referring now to FIG. 1, a sample acquiring device 10 according to a first embodiment will be described. The sample acquiring device 10 is preferably disposable and is to be thrown away after having been used for analysis. This implies that the sample acquiring device 10 does not require complicated handling. The sample acquiring device 10 is preferably formed in a plastic material and may be manufactured by injection-moulding. This makes manufacture of the sample acquiring device 10 simple and cheap, whereby the costs of the sample acquiring device 10 may be kept down.

The sample acquiring device 10 comprises a body member 12, which has a base 14, which may be touched by an operator without causing any interference in analysis results. The base 14 may also have projections 16 that may fit a holder in an analysis apparatus. The projections 16 may be arranged such that the sample acquiring device 10 will be correctly positioned in the analysis apparatus.

The sample acquiring device 10 further comprises a sample inlet 18. The sample inlet 18 is defined between opposite walls within the sample acquiring device 10, the walls being arranged so close to each other that a capillary force may be created in the sample inlet 18. The sample inlet 18 communicates with the exterior of the sample acquiring device 10 for allowing blood to be drawn into the sample acquiring device 10. The sample acquiring device 10 further comprises a chamber for counting white blood cells in the form of a measurement cavity 20 arranged between opposite walls inside the sample acquiring device 10. The measurement cavity 20 is arranged in communication with the sample inlet 18. The walls defining the measurement cavity 20 are arranged closer together than the walls of the sample inlet 18, such that a capillary force may draw blood from the sample inlet 18 into the measurement cavity 20.

The measurement cavity 20 has a first portion 20a having a first thickness and a second portion 20b having a second, smaller thickness. The first portion 20a is in communication with the sample inlet 18, whereas the second portion 20b is in communication with the first portion 20a. Thus, a capillary force may draw blood from the first portion 20a of the measurement cavity 20 into the second portion 20b.

The walls of the first portion 20a of the measurement cavity 20 are arranged at a distance from each other of 50-200 micrometers. The first portion 20a is more preferably at least 100 micrometers thick. Further, the first portion 20a is more preferably no more than 150 micrometers thick. The distance is generally uniform over the entire first portion 20a. The thickness of the first portion 20a defines the volume of blood being examined. Since the analysis result is to be compared to the volume of the blood sample being examined, the generally uniform thickness of the first portion 20a needs to be very precise, i.e. only very small variations in the thickness are allowed between first portions 20a of different sample acquiring devices 10. The thickness is chosen to allow a relatively large sample volume to be analysed in a small area of the cavity so that a sufficient number of particles or cells are available for counting. The first portion 20a of the measurement cavity 20 is specifically adapted for determining a volumetric total white blood cell count in a blood sample. The entire thickness of the first portion 20a may be chosen to allow it to be imaged within a depth of field of an imaging system. Then, an image may be analysed and the number of white blood cells present in the image may be counted in order to determine the volumetric white blood cell count.

The sample acquiring device 10 is typically adapted for measuring white blood cell counts above $0.5 \times 10^9$ cells/liter blood. At much lower white blood cell counts, the sample volume will be too small to allow statistically significant amounts of white blood cells to be counted. Further, when the white blood cell count exceeds $12 \times 10^9$ cells/liter blood, the effect of blood cells being arranged overlapping each other will start to be significant in the measured white blood cell count. At this white blood cell count, the white blood cells will cover approximately 8% of the cross-section of the sample being analyzed, if the thickness of the first portion 20a is 140 micrometers. Thus, in order to obtain correct white blood cell counts, this effect will need to be accounted for. Therefore, a statistical correction of values of the white blood cell count above $12 \times 10^9$ cells/liter blood may be used. This statistical correction will increase with increasing white blood cell counts, since the effect of overlapping blood cells increases with increased white blood cell counts. The statistical correction may be determined by means of calibration of a measurement apparatus. As an alternative, the statistical correction may be determined at a general level for setting up measurement apparatuses to be used in connection to the sample acquiring device 10. This statistical correaction is of similar magnitude as statistical corrections that are presently performed in analysis apparatus that use the Coulter principle. It is contemplated that the sample acquiring device 10 could be used to analyse white blood cell counts as large as $50 \times 10^9$ cells/liter blood.

The second portion 20b of the measurement cavity 20 is specifically adapted for determining a ratio of different types of white blood cells in a blood sample. The entire thickness of the second portion 20a is to be imaged within a depth of field of an imaging system. Then, an image may be analysed and the number of white blood cells of each type present in the image may be counted in order to determine the ratio of different types of white blood cells.

The walls of the second portion 20b of the measurement cavity 20 are arranged at a distance from each other of 20-60 micrometers. The distance is generally uniform over the entire second portion 20b. Since the analysis is mainly intended to compare the number of different types of white blood cells to each other, it is not critical to know the exact volume being analysed. Therefore, the thickness of the second portion 20b need not be as precise as the thickness of the first portion 20a. The thickness of the second portion 20b needs to allow a sufficient amount of white blood cells to be analysed in order to obtain statistically significant results. Further, as stated above the thickness of the second portion 20b should be adapted to be imaged in its entirety within a depth of field of an imaging system. Thus, all white blood cells within the sample are imaged in focus and the analysis of the sample is not hampered by noise in the image from parts of the sample imaged out of focus. The second portion 20b is thinner than the first portion 20a in order to enable a larger magnification to be used while allowing the entire second portion to be imaged within a depth of field of the imaging system. The larger magnification may be needed in order to allow not only counting the total number of white blood cells but also determining the type of white blood cells.

A surface of a wall of the measurement cavity 20 is at least partly coated with a reagent 22. The reagent 22 may be freeze-dried, heat-dried or vacuum-dried and applied to the surface of the measurement cavity 20. When a blood sample is acquired into the measurement cavity 20, the blood will make contact with the dried reagent 22 and initiate a reaction between the reagent 22 and the blood.

The reagent 22 is applied by inserting the reagent 22 into the measurement cavity 20 using a pipette or dispenser. The reagent 22 is solved in a volatile liquid, e.g. an organic solvent such as methanol, when inserted into the measurement cavity 20. The solvent with the reagent 22 may fill the measurement cavity 20. Then, drying is performed such that the solvent will be evaporated and the reagent 22 will be attached to the surfaces of the measurement cavity 20.

Since the reagent is to be dried onto a surface of a narrow space, the liquid will have a very small surface in contact with ambient atmosphere, whereby evaporation of the liquid is rendered more difficult. Thus, it is advantageous to use a volatile liquid, such as methanol, which enables the liquid to be evaporated in an effective manner from the narrow space of the measurement cavity.

According to an alternative manufacturing method, the sample acquiring device 10 may be formed by attaching two pieces to each other, whereby one piece forms the bottom wall of the measurement cavity 20 and the other piece forms the top wall of the measurement cavity 20. This allows a reagent 22 to be dried onto an open surface before the two pieces are attached to each other. Thus, the reagent 22 may be solved in water, since the solvent need not be volatile.

The reagent 22 comprises a red blood cell hemolysing agent and a white blood cell staining agent. The hemolysing agent may be a quaternary ammonium salt, a saponin, a bile acid, such as deoxycholic acid, a digitoxin, a snake venom, a glucopyranoside or a non-ionic detergent of type Triton. The staining agent may be Hematoxylin, Methylene blue, Methylene green, Methylene azure, cresyl violet acetate, Toluidine blue, Gentian violet, a Sudan analogue, Gallocyanine, or a Fuchsin analogue, or any combination thereof. When a blood sample makes contact with the reagent 22, the hemolysing agent will act to lyse the red blood cells such that the lysed red blood cells are mixed with the blood plasma. Further, the staining agent will accumulate in the nuclei of the white blood cells. The reagent 22 should contain sufficient amounts of staining agent to distinctly stain all the nuclei of the white blood cells. Thus, there will often be a surplus of staining agent, which will be intermixed in the blood plasma. The surplus of staining agent will give a homogenous, low background level of staining agent in the blood plasma. The accumulated staining agent in the white blood cells will be distinguishable over the background level of staining agent.

The reagent 22 may also comprise other constituents, which may be active, i.e. taking part in the chemical reaction with the blood sample, or non-active, i.e. not taking part in the chemical reaction with the blood sample. The active constituents may e.g. be arranged to catalyse the hemolysing or staining action. The non-active constituents may e.g. be arranged to improve attachment of the reagent 22 to the surface of a wall of the measurement cavity 20.

Within a few minutes or even less than a minute, the blood sample will have reacted with the reagent 22, such that the red blood cells have been lysed and the staining agent has accumulated in the nuclei of the white blood cells.

Figure 2:
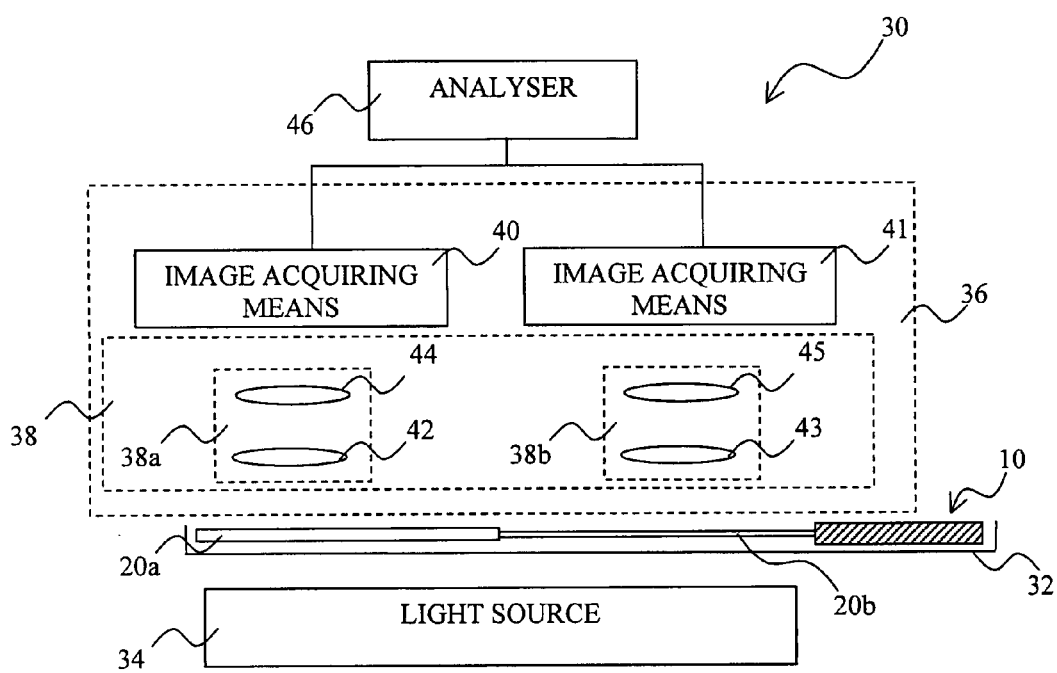
FIG. 2 is a schematic block diagram of a measurement apparatus according to a first embodiment.

Referring now to FIG. 2, a first embodiment of a measurement apparatus 30 for analysis of white blood cells in a blood sample will be described. The apparatus 30 comprises a sample holder 32 for receiving a sample acquiring device 10 with a blood sample. The sample holder 32 is arranged to receive the sample acquiring device 10 such that the measurement cavity 20 of the sample acquiring device 10 is correctly positioned within the apparatus 30. The apparatus 30 comprises a light source 34 for illuminating the blood sample within the sample acquiring device 10. The light source 34 may be an incandescent lamp, which irradiates light in the entire visible spectrum. The staining agent which is accumulated in the nuclei of the white blood cells will absorb light of specific wavelengths, such that the nuclei of the white blood cells will emerge in a digital image of the sample. If a colour image is acquired, the white blood cells will emerge as specifically coloured dots. If a black and white image is acquired, the white blood cells will emerge as dark dots against a lighter background.

The light source 34 may alternatively be a laser or a light emitting diode. This may be used for increasing contrast in the image such that the white blood cells may be more easily detected. In this case, the light source 34 is arranged to radiate electromagnetic radiation of a wavelength that corresponds to an absorption peak of the staining agent. The wavelength should further be chosen such that the absorption of the non-white blood cells components in the blood is relatively low. Further, the walls of the sample acquiring device 10 should be essentially transparent to the wavelength. For example, when Methylene blue is used as the staining agent, the light source 34 may be arranged to irradiate with light having a wavelength of 667 nm.

The apparatus 30 further comprises an imaging system 36, which is arranged on an opposite side of the sample holder 32 relative to the light source 34. Thus, the imaging system 36 is arranged to receive radiation which has been transmitted through the blood sample. The imaging system 36 in this embodiment comprises a magnifying means 38 that is divided into two separate parts. A first part 38a of the magnifying means 38 is arranged to receive radiation that has been transmitted through the blood sample in the first portion 20a of the measurement cavity 20. The imaging system further comprises a first image acquiring means 40, which is arranged to image the first portion 20a of the measurement cavity 20 as magnified by the first part 38a of the magnifying means 38. The first part 38a of the magnifying means 38 is arranged to provide a magnifying power of 1-50×, more preferably 1-20×, and most preferably 1-4×. Within these ranges of magnifying power, it is possible to distinguish the white blood cells. The image may be acquired with an improved resolution in order to allow lower magnifying power to be used. Further, the depth of field of the first part 38a of the magnifying means 38 may be arranged to include the thickness of the measurement cavity 20.

The first part 38a of the magnifying means 38 comprises an objective lens or lens system 42, which is arranged close to the sample holder 32, and an ocular lens or lens system 44, which is arranged at a distance from the objective lens 42. Each of the objective lens or lens system 42 and the ocular lens or lens system 44 may include one or a plurality of individual lenses or other optical components. The objective lens 42 provides a first magnification of the sample, which is further magnified by the ocular lens 44. The magnifying means 38 may comprise further lenses for accomplishing an appropriate magnification and imaging of the sample. The first part 38a of the magnifying means 38 is arranged such that the sample in the first portion 20a of the measurement cavity 20 when placed in the sample holder 32 will be focussed onto an image plane of the first image acquiring means 40.

The first image acquiring means 40 is arranged to acquire a first digital image of the sample. The first image acquiring means 40 may be any kind of digital camera, such as a CCD- or CMOS-camera. Reference to a digital camera as described herein should be considered as only one embodiment of an image analysis portion. The pixel size of the digital camera sets a restriction on the imaging system 36 such that the circle of confusion in the image plane may not exceed the pixel size within the depth of field. However, the white blood cells may still be detected even if they are somewhat blurred and, therefore, the circle of confusion may be allowed to exceed the pixel size while being considered within the depth of field, as defined in this context. As used herein, "depth of field" will thus imply a length in a direction along the optical axis that is imaged in a sufficient focus to allow image analysis to identify cells positioned within this length. This "depth of field" may be different from a conventional depth of field defined by the optical settings and may depend on the specific image analysis to be performed.

The digital camera 40 will acquire a first digital image of the sample in the first portion 20a of the measurement cavity 20, wherein the entire sample thickness is sufficiently focussed in the first digital image for counting the white blood cells. The imaging system 36 will define an area of the first portion 20a of the measurement cavity 20, which will be imaged in the first digital image. The area being imaged together with the thickness of the first portion 20a of the measurement cavity 20 defines the volume of the sample being imaged.

A second part 38b of the magnifying means 38 is arranged to receive radiation that has been transmitted through the blood sample in the second portion 20b of the measurement cavity 20. The imaging system further comprises a second image acquiring means 41, which is arranged to image the second portion 20b of the measurement cavity 20 as magnified by the second part 38b of the magnifying means 38. The second part 38b of the magnifying means 38 is arranged to provide a magnifying power of 5-200×, more preferably 5-100×, and most preferably 5-20×. Within these ranges of magnifying power, it is possible to distinguish between white blood cells. The image may be acquired with an improved resolution in order to allow lower magnifying power to be used. Further, the depth of field of the second part 38b of the magnifying means 38 may still be arranged to include the thickness of the measurement cavity 20.

Like the first part 38a, the second part 38b of the magnifying means 38 also comprises an objective lens or lens system 43, which is arranged close to the sample holder 32, and an ocular lens or lens system 45, which is arranged at a distance from the objective lens 43. Again, each of the objective lens or lens system 43 and the ocular lens or lens system 45 may include one or a plurality of lenses or other optical components. The objective lens 43 provides a first magnification of the sample, which is further magnified by the ocular lens 45. The magnifying means 38 may comprise further lenses or other optical components for accomplishing an appropriate magnification and imaging of the sample. The second part 38b of the magnifying means 38 is arranged such that the sample in the second portion 20b of the measurement cavity 20 when placed in the sample holder 32 will be focussed onto an image plane of the second image acquiring means 41.

The second image acquiring means 41 is arranged to acquire a second digital image of the sample. The second image acquiring means 41 may be any kind of digital camera, such as a CCD- or CMOS-camera. Since the second image is to be used for determining different types of white blood cells, the circle of confusion in the image plane may not exceed the pixel size within the depth of field. The digital camera 41 will acquire a second digital image of the sample in the second portion 20*a* of the measurement cavity 20, wherein the entire sample thickness is sufficiently focussed in the second digital image for identifying the type of the white blood cells present.

The imaging system 36 can be arranged for imaging blood samples in sample acquiring devices 10 without the need to adjust the imaging system 36. Preferably, the imaging system 36 is arranged within a housing which maintains the imaging system in a fixed relationship to the sample holder.

The apparatus 30 further comprises an image analyser 46. The image analyser 46 is connected to the first and second digital cameras 40, 41 for receiving first and second digital images acquired by the digital cameras 40, 41. The image analyser 46 is arranged to identify patterns in the first digital image that correspond to a white blood cell for counting the number of white blood cells being present in the digital image. Thus, the image analyser 46 may be arranged to identify dark dots in a lighter background. The image analyser 46 may be arranged to first electronically magnify the digital image before analysing the digital image. This implies that the image analyser 46 may be able to more easily distinguish white blood cells that are imaged closely to each other, even though the electronic magnifying of the digital image will make the digital image somewhat blurred.

The image analyzer 46 may include a processor adapted to receive image information from the first and second digital cameras 40, 41. The processor may be configured with image analysis software or algorithms, for example, the precise nature of which may be adapted to perform analyses as described herein.

The image analyser 46 may calculate the number of white blood cells per volume of blood by dividing the number of white blood cells being identified in the first digital image with the volume of the blood sample, which is well-defined as described above. The volumetric white blood cell count may be presented on a display of the apparatus 30.

The image analyser 46 is further arranged to identify patterns in the second digital image that correspond to a white blood cell for counting the number of white blood cells being present in the digital image. The image analyser 46 will further analyse the shape and size of each detected white blood cell in order to determine the type of the white blood cell. Thus, the image analyser 46 may be arranged to identify dark dots in a lighter background as white blood cells. The image analyser 46 may be arranged to first electronically magnify the digital image before analysing the digital image. This implies that the image analyser 46 may be able to more easily distinguish white blood cells that are imaged closely to each other, even though the electronic magnifying of the digital image will make the digital image somewhat blurred. The image analyser 46 will then determine the type of the white blood cell by various physical criteria, an important one being the size of the imaged white blood cell. In accordance with literature lymphocytes have a diameter of about 5-11 micrometers, granulocytes have a diameter of about 8-15 micrometers, and monocytes have a diameter of about 16-25 micrometers. Since the expected sizes in some cases overlap further information is preferably used to discriminate different white blood cell types from each other. Such information may e.g. be the shape and/or size of the nucleus. Granulocytes may e.g. be identified by presence of two or more dots within a cell corresponding to a segmented nucleus. This may be used to improve the assessment made by the size classification.

A white blood cell count differentiated in five parts, wherein the granulocytes are further differentiated as eosinophils, neutrophils and basophils, may be obtained by using further physical characteristics. Also, the three part white blood cell count may be improved using these additional physical characteristics. Thus, the analysis may further examine the shape of the detected blood cells. Also, the analysis may further examine an intensity of radiation transmitted through the detected blood cells.

The image analyser 46 may calculate the number of white blood cells of each type. Typically, the image analyser 46 may count and classify a certain number, e.g., 1000 white blood cells. The percentage or ratio of each type of white blood cells may then be determined as the number of white blood cells classified to belonging to the type divided with the total number of analysed white blood cells. A statistically significant measure may be determined by analysing about 200 white blood cells for type. However, it is desired that a larger number of white blood cells are analysed for type in order to improve statistics. Further, the image analyser 46 may be arranged to analyse white blood cells that are imaged in sufficient focus to be properly classified. Also, where two or more white blood cells are very close to each other, they may be difficult to separate correctly, and thus such white blood cells may be disregarded completely by the image analyser 46. On the other hand, since the imaging system 36 is arranged to image the entire thickness of the second portion 20*b* of the measurement cavity 20 in focus, the image analyser 46 may determine a volumetric enumeration of each type of white blood cells from the second digital image only.

The image analyser 46 may be realised as a processing unit, which comprises codes for performing the image analysis.

Figure 3:
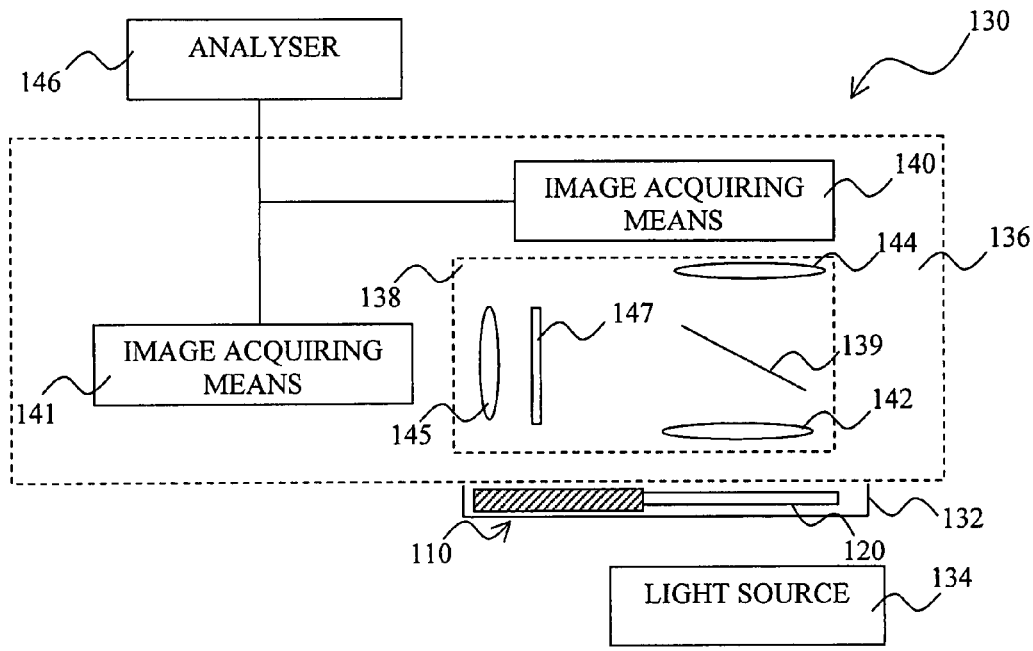
FIG. 3 is a schematic block diagram of a measurement apparatus according to a second embodiment.

Referring now to FIG. 3, a second embodiment of a measurement apparatus 130 for analysis of white blood cells in a blood sample will be described. The apparatus 130 comprises a sample holder 132 for receiving a sample acquiring device 110 with a blood sample. The apparatus 130 is arranged to receive sample acquiring devices 110, wherein the measurement cavity 120 has one uniform thickness over the entire area being imaged. Thus, the measurement cavity 120 has a thickness corresponding to the first portion 20*a* of the measurement cavity 20 of the sample acquiring device 10 according to the embodiment described above with reference to FIG. 1. The sample holder 132 is arranged to receive the sample acquiring device 110 such that the measurement cavity 120 of the sample acquiring device 110 is correctly positioned within the apparatus 130. The apparatus 130 comprises a light source 134 for illuminating the blood sample within the sample acquiring device 110 in a corresponding way as the light source 34 of the first embodiment.

The apparatus 130 further comprises an imaging system 136, which is arranged on an opposite side of the sample holder 132 relative to the light source 134. Thus, the imaging system 136 is arranged to receive radiation which has been transmitted through the blood sample. The imaging system 136 in this embodiment is arranged to acquire a first and a second digital image along the same optical path such that the images are centred at the same point in the measurement cavity 120. Still, the first and second digital images of the sample are acquired using different optical settings. This may be achieved in a number of different ways, as will be described below.

As shown in FIG. 3, the imaging system comprises a magnifying means 138 that comprises a common part and two separate parts. The magnifying means 138 may thus comprise an objective lens or lens system 142, which is arranged close to the sample holder 132 and which is shared for the two optical settings for acquiring both the first and the second digital images. The objective lens 142 provides a first magnification of the sample. The imaging system 136 may further comprise a beam splitter 139 for directing light in two different directions towards a first and a second image acquiring means 140, 141, which may be any kind of digital camera, such as a CCD-camera. The magnifying means 138 comprises a first ocular lens or lens system 144, which is arranged between the beam splitter 139 and the first digital camera 140. The objective lens 142 provides a first magnification of the sample, which is further magnified by the ocular lens 144. The magnifying means 138 may comprise further lenses or optical elements for accomplishing an appropriate magnification and imaging of the sample in the first digital image.

The magnifying means 138 further comprises a second ocular lens or lens system 145 may be, which is arranged between the beam splitter 139 and the second digital camera 141. The objective lens 142 provides a first magnification of the sample, which is further magnified by the ocular lens 145. The magnifying means 138 may comprise further lenses or optical elements for accomplishing an appropriate magnification and imaging of the sample in the second digital image. The objective lens 142 and the ocular lens 145 may be implemented as lens packages and the ocular lens package 145 will then move a virtual principal plane within the objective lens package 142 to change the relation between the image plane and the objective lens package 142 to allow the further magnification, while the sample acquiring device 110 is not moved in relation to the objective lens package 142. In this way, different magnifications may be obtained in the first and second digital images.

In particular, the magnifying means 138, as shown in this embodiment, comprises an optical element 147 that emphasizes imaging of white blood cells that are placed in focus. This enhances possibilities to identify which blood cells types are being imaged in focus and thereby are to be considered when distinguishing between different types of white blood cells.

The optical element 147 allows an image to be acquired of a sample thickness much larger than the depth of field of the part of the imaging system 136 that captures the second digital image. The optical element 147 ensures that the cells that are out of focus may be withdrawn from consideration in order to increase the certainty of the measurement. Since the optical element 147 affects the imaging of cells out of focus, the cells in focus will be easily identified. The optical element 147 may be implemented as a spatial filter that affects the imaging of a cell such that the edge of the cell will comprise an overshoot intensity larger than the background intensity, where the cell is imaged by absorbing light. This may easily be detected in image analysis and, therefore, these cells may be quickly discarded from consideration.

According to an alternative embodiment, the magnifying means may comprise a wavefront coding element between the beam splitter 139 and the second digital camera 141. The wavefront coding element may thus replace the optical element 147. A wavefront coding element deliberately distorts the light rays by passing them through a waveplate with a saddle-like shape, that is relatively flat in the middle, but with scalloped edges. This causes a specific optical aberration, the image looks blurry, but the de-focus is the same over a large range of distances. This wavefront coding element thus increases a depth along the optical axis that may be analysed. The distortions in the image are mainly determined by the shape of the de-focusing wavefront coding element, which is accurately known. Therefore, a computer is able to remove the blur point by point. A computer may decode the image using what is essentially a digital filter, and thus create an image which is sharp over a large depth of field. In this way, the magnifying means may increase the depth of field of the imaging system, enabling a larger depth of a sample to be imaged in focus.

In this embodiment, the beam splitter may be replaced with, the image system 136 may comprise a mirror or other element (not shown) for directing essentially all light from the sample towards a selected one of the two digital cameras 140, 141. The mirror may then be turned or moved for shifting the camera 140, 141 that is viewing the sample. This allows more light to pass to the digital cameras 140, 141 and thus gives better light conditions for acquiring the images. However, the two images may not be recorded simultaneously and the image system 136 will need moving parts. According to one alternative, one of the cameras may be arranged to view the sample when the mirror is completely removed from the optical path.

According to another alternative, the objective lens 142 may provide all magnification needed for obtaining the first image. Thus, light may be passed directly from the beam splitter or mirror to the first digital camera 140.

According to yet another alternative, no objective lens is shared by the first and second optical settings. Thus, a beam splitter or mirror may be arranged close to the sample holder 132 and the magnifying means 138 may comprise both an objective lens and an ocular lens in both optical paths between the beam splitter and the first digital camera 140 and between the beam splitter and the second digital camera 141.

Figure 5:
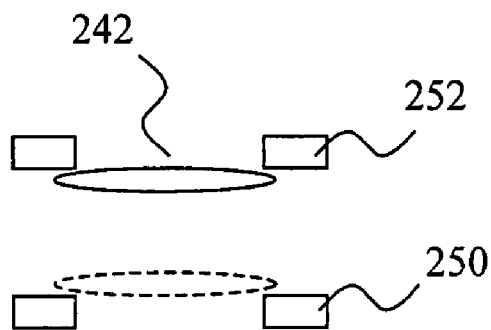
FIG. 5 is a schematic view of an arrangement for a movable lens according to an embodiment of the invention.

According to a further alternative, the first and second digital images are obtained by means of one digital camera. In this case, the magnifying means 138 needs to be switched or changed in order to change the optical settings for obtaining the two digital images. Thus, an objective lens 242 may be movable between two different well-defined positions, as shown in FIG. 5. The objective lens 242 may thus be arranged to be moved along the optical axis and will make contact with a stop, e.g. an edge of the optical axis making contact with a protrusion 250, 252. The distance between the objective lens and the sample acquiring device may thus be accurately controlled for controlling the magnification of an image to be acquired.

In any of the above described alternatives, the first digital camera 140 is arranged to image the measurement cavity 120 with a first optical setting provided by the magnifying means 138. The magnifying means 138 is thus arranged to provide a magnifying power of 1-50×, more preferably 1-20×, and most preferably 14×. Within these ranges of magnifying power, it is possible to distinguish the white blood cells. The image may be acquired with an improved resolution in order to allow lower magnifying power to be used. Further, the depth of field of the magnifying means 138 may still be arranged to include the thickness of the measurement cavity 120.

As described with reference to the first embodiment shown in FIG. 2, the first digital camera 140 in the second embodiment is arranged to acquire a first digital image of the sample. The first digital camera 140 views the sample such that the entire thickness of the measurement cavity 120 is within the depth of field as defined for the first embodiment. The imaging system 136 will define an area of the measurement cavity 120, which will be imaged in the first digital image. The area being imaged together with the thickness of the measurement cavity 120 defines the volume of the sample being imaged.

Further, in any of the above described embodiments, the second digital camera 141 is arranged to image the measurement cavity 120 with a second optical setting provided by the magnifying means 138. The magnifying means 138 is arranged to provide a magnifying power of 5-200×, more preferably 5-100×, and most preferably 5-20×. Within these ranges of magnifying power, it is possible to distinguish the white blood cells. The image may be acquired with an improved resolution in order to allow lower magnifying power to be used. However, since the second digital image views the same part of the measurement cavity 120 as the first digital image, the greater magnification used in the second optical setting may prevent the entire thickness of the measurement cavity 120 from being imaged within a depth of field. The second digital image will thus image white blood cells in focus, but will also image white blood cells and other parts of the blood sample that are out of focus causing a blurring disturbance in the image. In these conditions, the optical element 147, as described above, will improve the chances to identify cells that are imaged in focus making easier to classify as to type.

The magnifying means 138 may advantageously be arranged to place a top portion of the thickness of the measurement cavity 120 in focus in the image plane of the second digital camera 141. This implies that the disturbances of the parts of the blood sample that are out of focus are near the bottom and remain relatively low. However, it is conceivable that any portion of the measurement cavity 120 is imaged in focus in the second digital image. Further, the magnifying means 138 may be arranged to typically image a thickness of 20-60 micrometers of the measurement cavity 120 in focus.

Figure 6:
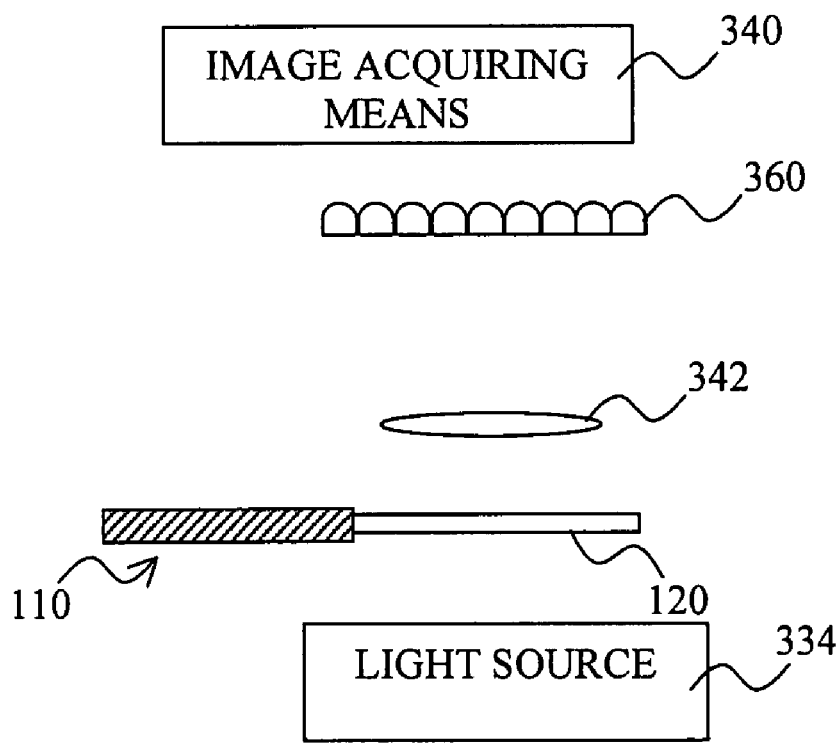
FIG. 6 is a schematic view of an arrangement according to an embodiment of the invention.

According to yet another alternative, as illustrated in FIG. 6, only one digital image is acquired. However, this digital image needs to provide information of the direction of light being detected. This implies that the digital image contains information of not only the detected radiation, but also a point in space from which the detected radiation was emitted. This digital image may then be presented in such a way that the focus of the digital image may be shifted as desired. The digital image may thus be used firstly to count a total number of white blood cells within the entire depth of the measurement cavity and secondly, by shifting focus to a portion of the thickness, to determine the ratio of different types of white blood cells in the sample. This alternative may be implemented as shown in FIG. 6 comprising a light source 334, an objective lens 342 and one digital camera 340. These parts may be implemented in a similar way as described above. The apparatus further comprises an array of small lenses 360 being provided in the optical path between the sample acquiring device 110 and the digital camera 340. The array of small lenses 360 provides a possibility to trace rays in the acquired image such that different parts of the image may be placed in focus.

Returning now to FIG. 3, the apparatus 130 further comprises an image analyser 146. The image analyser 146 is connected to the first and second digital cameras 140, 141 for receiving first and second digital images acquired by the digital cameras 140, 141. Alternatively, the image analyser 146 receives only one digital image containing information of direction of light as described in the above paragraph. The image analyser 146 is arranged to analyse the first and second digital images in a similar way as described for the image analyser 46 of the first embodiment above. However, since the second digital image may be obtained by imaging only part of the thickness of the sample within a depth of field, the image analyser 146 may need to handle the second digital image more carefully. First of all, the image analyser 146 will only analyse white blood cells that are identified to be imaged in focus. This is possible since the image analyser 146 may only determine the ratio of different types of white blood cells and will therefore not need to exactly know the volume of the sample being analysed. Cells that are imaged out of focus may be blurred in such a way that the image analyser 146 could determine incorrect sizes of the cells and therefore incorrectly classify the cells. Thus, by ensuring that only cells that are imaged in focus are analysed, the certainty of the analysis is improved.

FIG. 7 illustrates a sample 710 imaged at three different layers 720a-c of the sample 710. Layer 720b indicates a focus plane to be discussed in detail below. An optic system has a depth of field in which objects may be considered to be in focus even if they are not positioned exactly in the focus plane. In FIG. 7 the depth of field of focus plane 720b is indicated by the dashed area 720b'.

FIGS. 8a-c illustrate three different white blood cells in camera view and FIG. 9a-c illustrate their respective light distributions.

FIG. 8b illustrates a white blood cell imaged in focus. The nuclei appear as dark shadows whereas the surrounding cytoplasm is almost invisible. In FIG. 9b the distribution of light intensity is shown. The nuclei appear as portions with significantly lower light intensity whereas the cytoplasm leaves the light intensity unaffected.

FIG. 8a illustrates a white blood cell imaged too close to the image acquiring means 441 to be in focus. The nuclei appear as dark shadows whereas the surrounding cytoplasm acts as a lens and refracts and diffuses the light which results in a dark circle around the nuclei. In FIG. 9a the distribution of light intensity is shown. The nuclei appear as a portion with significantly lower light intensity and the cytoplasm appears with low light intensity.

FIG. 8c illustrates a white blood cell imaged too far away from the image acquiring means 441 to be in focus. The nuclei appear as dark shadows whereas the surrounding cytoplasm acts as a lens and refracts the light resulting in a bright circle around the nuclei. In FIG. 9c the distribution of light intensity is shown. The nuclei appear as a portion with significantly lower light intensity whereas the cytoplasm appears with high light intensity.

The image analyser 146 is further arranged to determine the size of the white blood cells imaged in focus. This determined size may then be used to classify the white blood cells in a manner corresponding to the manner described above with reference to the first embodiment. Since the second digital image may be a bit blurry and difficult to analyse, the image analyser 146 may be arranged to count and classify only a relatively small number, 200 say, of white blood cells. This may still be sufficient for forming a statistically significant result of the ratio of different types of white blood cells in the sample. As an alternative, the image analyser 146 may be arranged to perform measurement of size and verification whether a cell is imaged in focus within the same image processing step. Thus, the size of every imaged cell is determined, but only the cells that are imaged in focus are considered when determining the ratio of different types of white blood cells in the sample.

The image analyser 146 may be realised as a processing unit, which comprises codes for performing the image analysis.

Figure 10:
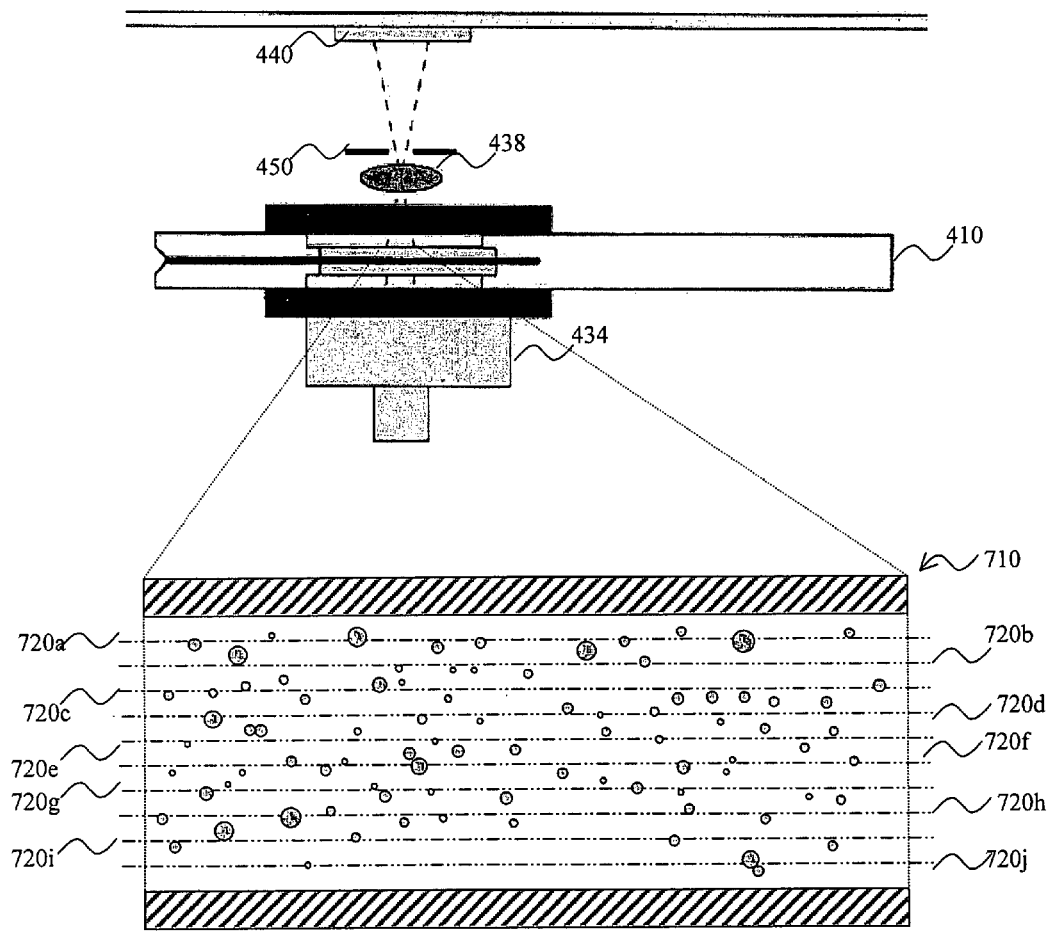
FIG. 10 is a schematic view of a measurement apparatus according to a third embodiment.

When using the principal of FIG. 7-9a-c and the setup of FIG. 10 the apparatus 30 may be arranged to acquire several digital images of the sample using different optical settings. For example, the several digital images may image ten different layers 720a-j of the sample 710 as shown in FIG. 10.

The image analyser is arranged to, for a specific particle or cell, determine the number of said images in which said particle or cell is imaged. The counting of images starts from an image in which the particle or cell is determined to be out of focus in a first direction continues via the image(s) in which the particle or cell is determined to be in focus and ends in an image in which the particle or cell is determined to be out of focus in a second direction. The first and second directions are basically opposite normals to the focus plane. In FIG. 8a and FIG. 9a the cell is determined to be out of focus in a first direction. The limit for being out of focus in this direction is determined to be the image in which the greatest contrast is measured for a specific cell for the different areas (central and ring area). For cells being located even closer to the imaging system the same basic shape with a dark ring around a dark nuclei will be detected, but the they will be more blurred and the contrast will be lower than in the image determined as the limit for being out of focus in the first direction. Similarly will the other limit be determined by identifying in which image the greatest contrast between the dark nuclei and the light encircling the nuclei is detected. In the images with a focus plane even further from the imaging system, the cells will still be detected as a dark nuclei and a light circle, but the they will be more blurred and the contrast will be lower than in the image that is considered as the limit for being out of focus in the second direction.

This will give information concerning the radius of curvature of the respective white blood cell. A comparably small white blood cell will give a comparably short focus length and will, when counting images between the limiting images, result in a comparably low number of images. This may also be said as that they move quickly in and out of focus. A comparably large white blood cell will give a longer focus length and the distance between the image in which they are out of focus in one direction and the image in which they are out of focus in the other direction will be comparably greater. This may also be said as that they will move slowly in and out of focus when comparing the different acquired images with images from neighbouring layers. It may be noted that the focus length and the limiting images relate to a distance, but with a specified distance in focus plane for respective image a distance may instead be denoted as a number of images.

Figure 4:
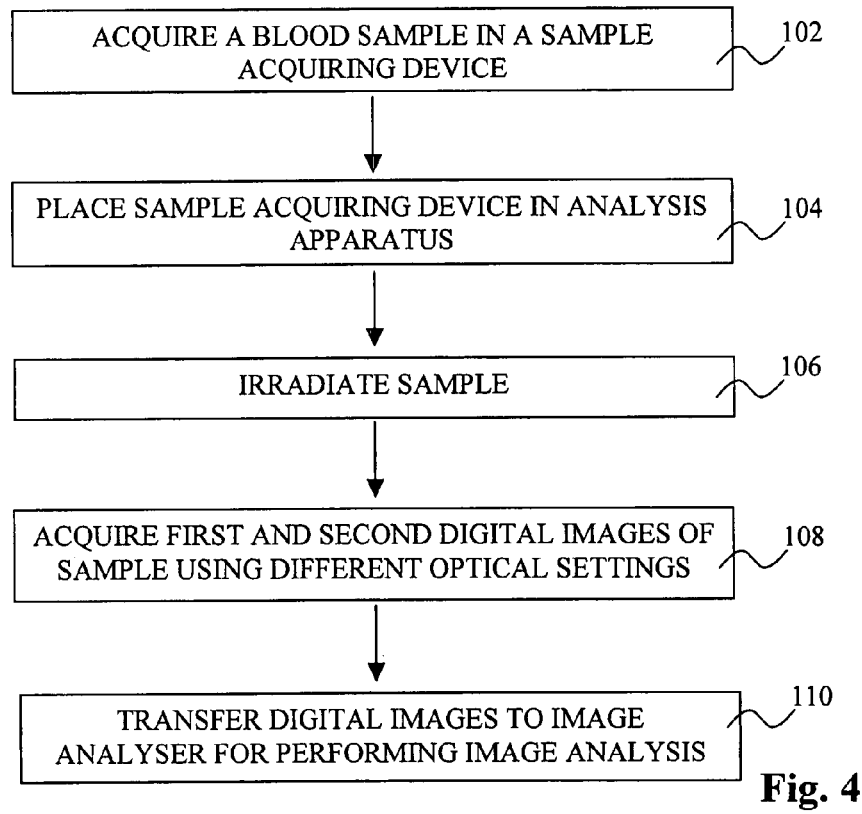
FIG. 4 is a flow chart of a method according to a first embodiment of the invention.

The embodiment of FIG. 10 comprises a light source 434, a sample acquiring device 410, an optical system 438 (with a magnification factor of 10×), a diaphragm 450 directing the light to an image acquiring means 440. Referring to FIG. 4, a method for volumetric enumeration of white blood cells will be described. The method comprises acquiring a blood sample in a sample acquiring device, step 102. An undiluted sample of whole blood is acquired in the sample acquiring device. The sample may be acquired from capillary blood or venous blood. A sample of capillary blood may be drawn into the measurement cavity directly from a pricked finger of a patient. The blood sample makes contact with a reagent in the sample acquiring device initiating a reaction. The red blood cells will be lysed and a staining agent is accumulated in the nuclei of the white blood cells. Within a few minutes from acquiring the blood sample, the sample is ready to be analysed. Alternatively, a blood sample is acquired and mixed with a hemolysing agent and a staining agent before being introduced into the sample acquiring device. The sample acquiring device is then placed in an analysis apparatus, step 104. An analysis may be initiated by pushing a button of the analysis apparatus. Alternatively, the analysis is automatically initiated by the apparatus detecting the presence of the sample acquiring device.

The sample is irradiated, step 106, and a first and a second digital image of the sample is acquired, step 108, using different optical settings. The sample is being irradiated with electromagnetic radiation of a wavelength corresponding to an absorption peak of the staining agent. This implies that the digital images will contain black or darker dots in the positions of the white blood cell nuclei.

The acquired digital images are transferred to an image analyser, which performs image analysis of the first and second digital images, step 110. The image analyser counts the number of black dots in the first digital image in order to determine a volumetric enumeration of all white blood cells in the blood sample. The image analyser also analyses the size and shape of a certain number of black dots in the second digital image in order to classify the white blood cells and obtain a ratio of different types of white blood cells in the blood sample.

Figure 11:
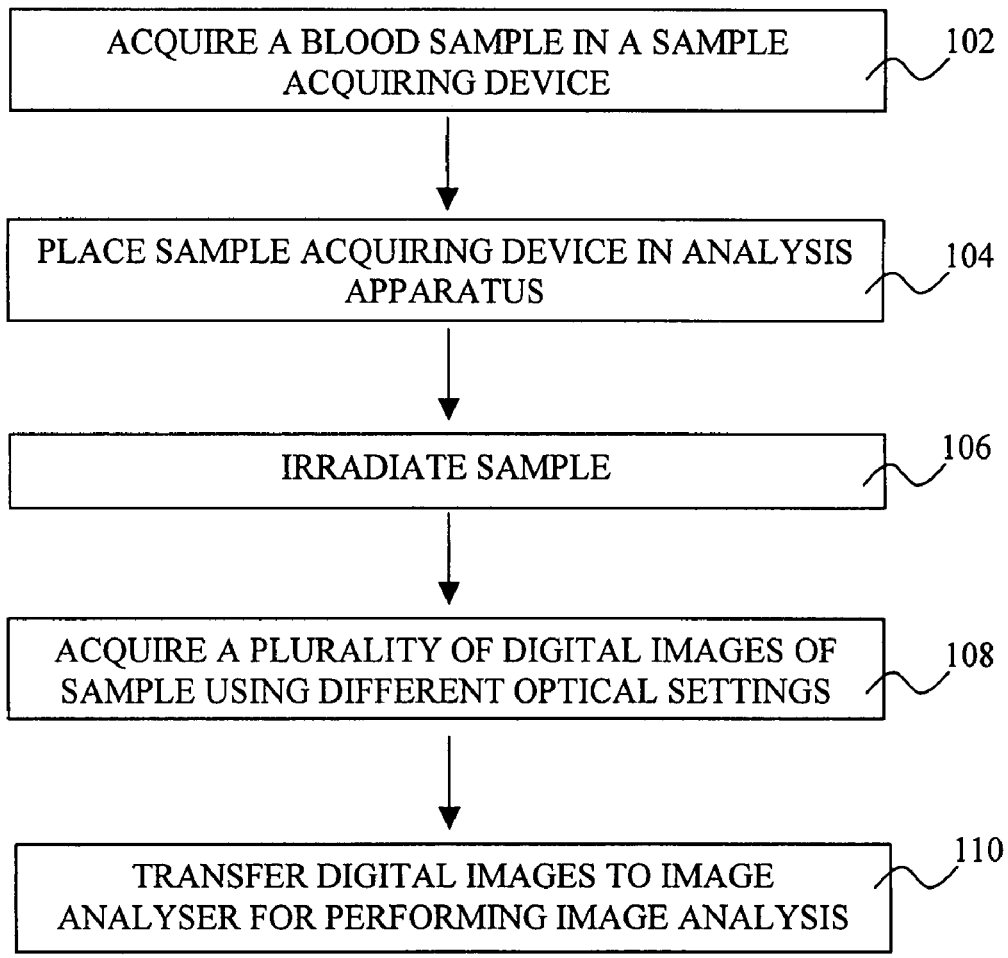
FIG. 11 is a flow chart of a method according to a second embodiment of the invention.

According to another embodiment illustrated in FIG. 11, the image acquiring step 108b involves acquiring a plurality of digital images at different layers.

In the image analyser the respective digital image (from each layer) is analysed in order to determine which white blood cells are in focus and for these white blood cells the image is analysed to classify the white blood cells and obtain a ratio of different types of white blood cells in the blood sample.

It should be emphasized that the preferred embodiments described herein are in no way limiting and that many alternative embodiments are possible within the scope of protection defined by the appended claims.

Figure 12:
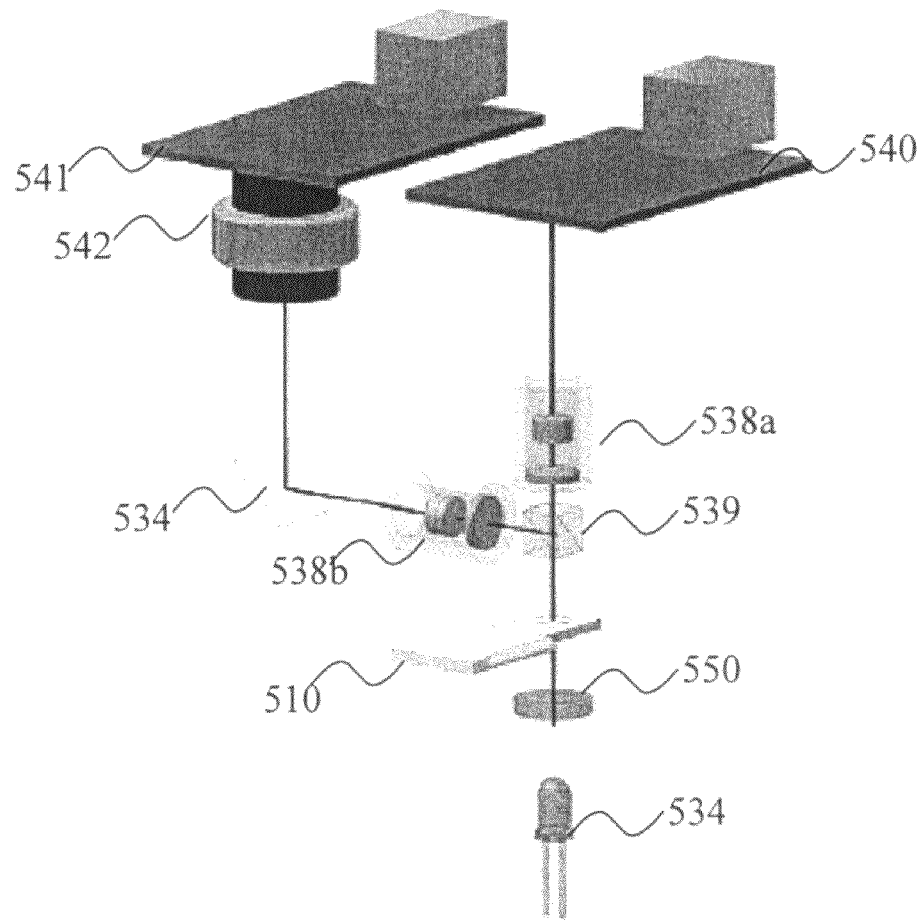
FIG. 12 is a schematic view of a measurement apparatus according to a fourth embodiment.

The apparatus of FIG. 10 may be a separate unit since the total number of white blood cells may be determined while determining the classification of respective white blood cell. Alternatively the apparatus of FIG. 10 may be used as image acquiring means 41 in the embodiment of FIG. 2 or as image acquiring means 141 in the embodiment of FIG. 3. Such a design is in principle shown in FIG. 12. This embodiment comprises a light source 534, a diaphragm 550, a sample acquiring device 510, a beam splitter 539, a first optical system 538a (with a first magnification factor of about 3×) directing the light to a first image acquiring means 540 and a second optical system 538b (with a second magnification factor of about 10×) directing the light to a second image acquiring means 541 via a mirror 534. The second optical system also comprises means for changing the focus 542 or may be movable. Thereby the second acquiring means 541 is capable of acquiring a plurality of digital images. In one embodiment the first image acquiring means 540 is omitted and the total number of particles or white blood cells is determined from the images acquired by the second image acquiring means 541.

The invention claimed is:

1. A measurement apparatus for enumeration of white blood cells in a sample, the apparatus comprising:
   a holder, which is arranged to receive a sample acquiring device comprising a measurement cavity that holds a sample, wherein the measurement cavity is adapted to hold a stained and hemolysed sample, and wherein the measurement cavity has a uniform depth of 50-200 micrometers,
   an imaging system adapted to acquire a plurality of digital images of the sample at different levels in a direction of depth of field in the sample using different optical settings, wherein the imaging system is arranged to obtain said digital images with a depth of field in the range of 2-30 micrometers, and an image analyzer, which is arranged to analyze each of the acquired plurality of digital images for identifying stained white blood cells and determining the number of white blood cells in the sample, wherein the image analyzer is arranged to analyze each of the acquired plurality of digital images for identifying white blood cells that are imaged in focus and determining types and number of the white blood cells that are imaged in focus, the types being distinguished by physical features of the stained white blood cells, whereby the ratio of different types of white blood cells in the sample is determined;

wherein a white blood cell in an image is determined to be in focus when a value of a property of the image white blood cell falls within a predetermined range;

wherein the image analyzer is arranged to, for a specific white blood cell, determine the number of said images in which said white blood cell is imaged counting from an image in which the white blood cell is determined to be out of focus in a first direction, to an image in which the white blood cell is determined to be out of focus in a second direction;

wherein determining the types and number of the white blood cells that are imaged in focus is based at least in part on the number of images.

2. The measurement apparatus according to claim 1, further comprising an electromagnetic radiation source, which is arranged to irradiate the sample held in the measurement cavity of the sample acquiring device.

3. The measurement apparatus according to claim 1, wherein the imaging system is arranged to provide information of direction of light in an acquired image, whereby shifting focus in the acquired image is enabled.

4. The measurement apparatus according to claim 1, wherein the image analyzer is arranged to analyze edges of imaged white blood cells in order to assess whether a white blood cell is imaged in focus based on a slope of intensity at the edge.

5. The measurement apparatus according to claim 1, wherein the image analyzer is arranged to determine, based on the counted number of images, a physical feature related to the size of said white blood cell.

6. The measurement apparatus according to claim 1, wherein the imaging system with the optical settings used for acquiring said plurality of digital images has a magnification power of 1-50×.

7. The measurement apparatus according to claim 2, wherein the electromagnetic radiation source is arranged to irradiate with a wavelength of light corresponding to a peak in absorbance of a staining agent.

8. The measurement apparatus according to claim 2, wherein said electromagnetic radiation source comprises a laser source.

9. The measurement apparatus according to claim 2, wherein said electromagnetic radiation source comprises a light emitting diode.

10. The measurement apparatus according to claim 1, wherein the image analyzer is arranged to identify areas of high light absorbance in order to determine the number of the white blood cells in the sample.

11. The measurement apparatus according to claim 10, wherein the image analyzer is arranged to identify dark dots in order to determine the number of the white blood cells in the sample.

12. The measurement apparatus according to claim 1, wherein the image analyzer is arranged to distinguish different types of white blood cells by analyzing shape and size of identified areas of high light absorbance in at least one of the plurality of digital images.

13. A method for enumeration of white blood cells in a sample, said method comprising:

acquiring a sample into a measurement cavity of a sample acquiring device, the sample being mixed with a reagent, comprising a hemolysing agent for lysing red blood cells in the sample and a staining agent for staining white blood cells in the sample, wherein the measurement cavity has a uniform depth of 50-200 micrometers, acquiring a plurality of digital images of an irradiated sample in the measurement cavity at different levels in a direction of depth of field in the sample using different optical settings, wherein the imaging system is arranged to obtain said plurality of digital images with a depth of field in the range of 2-30 micrometers, digitally analyzing each of the acquired plurality of digital images for identifying the stained white blood cells and determining the number of white blood cells in the sample, and digitally analyzing each of the acquired plurality of digital images for identifying stained white blood cells that are imaged in focus and determining types and number of the white blood cells that are imaged in focus, the types being distinguished by physical features of the white blood cells that are imaged in focus, whereby the ratio of different types of white blood cells in the sample is determined;

wherein a white blood cell in an image is determined to be in focus when a value of a property of the imaged white blood cell falls within a predetermined range;

wherein the image analysis comprises, for a specific white blood cell, determining the number of said images in which said white blood cell is imaged counting from an image in which the white blood cell is determined to be out of focus in a first direction, to an image in which the white blood cell is determined to be out of focus in a second direction;

wherein determining the types and number of the white blood cells that are imaged in focus is based at least in part on the number of images.

14. The method according to claim 13, wherein the sample is mixed with the reagent in the measurement cavity.

15. The method according to claim 13, wherein, based on the counted number of images, a physical feature related to the size of said cell is determined.

16. The method according to claim 13, wherein said plurality of digital images is acquired using a magnification power of 1-50×.

17. The method according to claim 13, wherein the sample is irradiated by light of a wavelength corresponding to a peak in absorbance of the staining agent.

18. The method according to claim 17, wherein said irradiating is performed by means of a laser source.

19. The method according to claim 17, wherein said irradiating is performed by means of a light emitting diode.

20. The method according to claim 13, wherein said analyzing comprises identifying areas of high light absorbance in order to determine the number of the white blood cells in the sample.

21. The method according to claim 20, wherein said analyzing comprises identifying dark dots in order to determine the number of the white blood cells in the sample.

22. The method according to claim 13, wherein said analyzing comprises distinguishing different types of white blood cells by analyzing shape and size of identified areas of high light absorbance in the at least one digital image.

23. A non-transitory computer-readable medium storing a computer program product, which causes a computer to execute a method for enumeration of white blood cells in a sample, said method comprising:
    digitally analyzing a plurality of images of a sample for determining a number of white blood cells in the sample; wherein the sample is acquired into a measurement cavity of a sample acquiring device; wherein the measurement cavity has a uniform depth of 50-200 micrometers; wherein the plurality of digital images of an irradiated sample in the measurement cavity is acquired at different levels in a direction of depth of field in the sample using different optical settings with a depth of field in the range of 2-30 micrometers;
    digitally analyzing each of the plurality of images of the sample for identifying one or more types of white blood cells in a focused region of the sample, each type of white blood cells being associated with one or more distinguishing physical features; and
    outputting information corresponding to the number and types of white blood cells in the sample;
    wherein a white blood cell in an image is determined to be in focus when a value of a property of the imaged white blood cell falls within a predetermined range;
    wherein the image analyzer is arranged to, for a specific white blood cell, determine the number of said images in which said white blood cell is imaged counting from an image in which the white blood cell is determined to be out of focus in a first direction, to an image in which the white blood cell is determined to be out of focus in a second direction;
    wherein determining the types and number of the white blood cells that are imaged in focus is based at least in part on the number of images.

24. A non-transitory computer-readable medium storing a computer program which causes a computer to execute a method of analyzing a sample, the computer program comprising:
    analyzing a plurality of digital images for identifying white blood cells and determining the number of white blood cells in the sample; wherein the sample is acquired into a measurement cavity of a sample acquiring device; wherein the measurement cavity has a uniform depth of 50-200 micrometers; wherein the plurality of digital images of an irradiated sample in the measurement cavity is acquired at different levels in a direction of depth of field in the sample using different optical settings with a depth of field in the range of 2-30 micrometers; and
    analyzing the plurality of digital images for identifying white blood cells that are imaged in focus and determining types and number of the white blood cells imaged in focus, the types being distinguished by physical features of the white blood cells imaged in focus, whereby the ratio of different types of the white blood cells in the sample is determined;
    wherein a white blood cell in an image is determined to be in focus when a value of a property of the imaged white blood cell falls within a predetermined range;
    wherein the image analyzer is arranged to, for a specific white blood cell, determine the number of said images in which said white blood cell is imaged counting from an image in which the white blood cell is determined to be out of focus in a first direction, to an image in which the white blood cell is determined to be out of focus in a second direction;
    wherein determining the types and number of the white blood cells that are imaged in focus is based at least in part on the number of images.

* * * * *